United States Patent
Robbins

(10) Patent No.: US 12,426,926 B2
(45) Date of Patent: Sep. 30, 2025

(54) HYBRID APPROACH METHODS FOR SACROILIAC JOINT STABILIZATION

(71) Applicant: Joseph Robbins, Vestavia Hills, AL (US)

(72) Inventor: Joseph Robbins, Vestavia Hills, AL (US)

(*) Notice: Subject to any disclaimer, the term of this patent is extended or adjusted under 35 U.S.C. 154(b) by 118 days.

(21) Appl. No.: 18/531,427

(22) Filed: Dec. 6, 2023

(65) Prior Publication Data

US 2024/0180595 A1    Jun. 6, 2024

Related U.S. Application Data

(60) Provisional application No. 63/430,532, filed on Dec. 6, 2022.

(51) Int. Cl.
*A61B 17/70* (2006.01)
*A61B 17/17* (2006.01)
*A61F 2/30* (2006.01)

(52) U.S. Cl.
CPC ...... *A61B 17/7055* (2013.01); *A61B 17/1757* (2013.01); *A61F 2/30988* (2013.01); *A61F 2002/30995* (2013.01)

(58) Field of Classification Search
CPC ............. A61B 17/7055; A61B 17/1757; A61F 2002/30995
See application file for complete search history.

(56) References Cited

U.S. PATENT DOCUMENTS

| | | | |
|---|---|---|---|
| 5,334,205 A | 8/1994 | Cain | |
| 6,053,916 A * | 4/2000 | Moore | A61F 2/30988 606/86 R |
| 8,388,667 B2 * | 3/2013 | Reiley | A61B 17/8695 606/301 |
| 8,778,026 B2 * | 7/2014 | Mauldin | A61F 2/30988 606/53 |
| 8,882,818 B1 * | 11/2014 | Vestgaarden | A61B 17/1662 623/17.11 |
| 9,186,155 B2 | 11/2015 | Katzman et al. | |
| D816,843 S | 5/2018 | Lewis | |
| 11,553,953 B1 | 1/2023 | Robbins | |
| 11,607,256 B1 | 3/2023 | Folsom et al. | |
| 2008/0009861 A1 | 1/2008 | Stark | |
| 2008/0097436 A1 | 4/2008 | Culbert et al. | |
| 2009/0149857 A1 | 6/2009 | Culbert et al. | |

(Continued)

*Primary Examiner* — Christian A Sevilla
(74) *Attorney, Agent, or Firm* — C. Brandon Browning; Maynard Nexsen PC

(57) ABSTRACT

A lateral-posterior approach sacroiliac joint stabilizing method including, as viewed from a lateral view of a pelvic region of a prone patient, forming a first incision that is anterior to a posterior sacral wall and inferior to an ala and a second incision that is located along a lateral border of the sacroiliac joint, and thereafter, forming a first void that extends from the first incision, through the ilium, across the sacroiliac joint and into the sacrum and a second void that extends between the second incision and into the sacroiliac joint. A first implant is placed within the first void such that the first implant extends across the sacroiliac joint with its distal end within the sacrum and its proximal end flush with the lateral aspect of the ilium, and a second implant is placed within the second void such that the second implant extends into the sacroiliac joint.

20 Claims, 20 Drawing Sheets

(56) References Cited

U.S. PATENT DOCUMENTS

| | | |
|---|---|---|
| 2009/0216238 A1* | 8/2009 | Stark .................... A61F 2/4657 |
| | | 606/329 |
| 2011/0087294 A1 | 4/2011 | Reiley |
| 2011/0087296 A1 | 4/2011 | Reiley et al. |
| 2011/0166575 A1 | 7/2011 | Assell et al. |
| 2011/0238181 A1 | 9/2011 | Trieu |
| 2012/0010620 A1 | 1/2012 | Petersen |
| 2012/0232658 A1 | 9/2012 | Morgenstern Lopez et al. |
| 2012/0310348 A1 | 12/2012 | Pafford et al. |

* cited by examiner

HYBRID APPROACH METHODS FOR SACROILIAC JOINT STABILIZATION

RELATED REFERENCES

This application claims priority to U.S. Provisional Patent Application No. 63/430,532 for "Hybrid Approach Methods for Sacroiliac Joint Stabilization," filed on Dec. 6, 2022, the entire contents of which are incorporated herein by reference.

BACKGROUND OF INVENTION

The sacroiliac joints are located between the ilia and sacrum bones and function to support the weight of the upper body. However, disorders or injury can cause joint pain, degeneration, and fracture. For instance, sacroiliitis occurs when there is inflammation in one or both sacroiliac joints leading to pain in the back, buttocks, or thighs. This condition may be caused by abnormal motion in the sacroiliac joint. Changes to ligament support to the sacroiliac joint are also sources of sacroiliac joint pain, such as ligament support variation during the hormonal changes from menstruation and pregnancy. Further, the sacroiliac joint is susceptible to trauma, which may result in joint injury or instability.

Several non-surgical treatments for sacroiliac joint injury or disorders exist, including administration of steroids or pain medication, exercise, rehabilitation, and complementary medicine. However, these treatments often provide only temporary pain relief and must be repeatedly administered. An alternative to such treatments is immobilization of the sacroiliac joint through surgical means, such as through use of hardware or other surgical components to span the joint. Therefore, methods that improve the effectiveness of sacroiliac joint stabilization, reduce incidences of significant surgical complications, and avoid infection are desired.

SUMMARY OF THE INVENTION

The present disclosure is directed to a hybrid lateral and posterior approach for stabilizing the sacroiliac joint. In a first aspect of the present disclosure, there is provided a method of stabilizing a sacroiliac joint of a patient through a hybrid lateral-posterior approach. The method includes first making a first incision for a lateral approach, the first incision located anterior to a posterior sacral wall and inferior to an ala as viewed from a lateral view of a pelvic region of the patient in prone position. A first initial void is formed between the first incision and a lateral aspect of an ilium. A lateral introducer is then advanced through the first initial void, through the ilium, across a sacroiliac joint, and into a sacrum. Then, a first intermediate void that is larger in diameter than the first initial void is formed by advancing at least one lateral dilator over the lateral introducer to the lateral aspect of the ilium. A first final void is formed by extending from the first intermediate void, through the ilium and sacroiliac joint, and into the sacrum, the first final void having a sacral extension depth appropriate for reception of a transfixing implant. The transfixing implant is then placed within the first final void so that the transfixing implant extends across the sacroiliac joint with its distal end within the sacrum and its proximal end flush with the lateral aspect of the ilium.

The method further includes making a second incision for a posterior approach, the second incision located along a lateral border of the sacroiliac joint as viewed from an anterior-posterior view of the pelvic region of the patient in prone position. A second initial void is formed between the second incision and the sacroiliac joint. An intra-articular introducer is advanced through the second initial void and into the sacroiliac joint. Then, a second intermediate void that is larger in diameter than the second initial void is formed by advancing at least one intra-articular dilator over the intra-articular introducer and into the sacroiliac joint. A second final void that expands the second intermediate void is formed within the sacroiliac joint, the second final void having a sacroiliac joint extension depth appropriate for reception of an intra-articular implant. The intra-articular implant is then placed within the second final void so that the intra-articular implant extends into the sacroiliac joint, and so that the sacroiliac joint is stabilized by the transfixing implant and the intra-articular implant.

In some instances, the first incision and the second incision are each 1 cm in length. In some instances, the transfixing implant is threaded and contains a central channel to collect bone chips and integrate bone in-growth, or the transfixing implant is coated with a pro-growth coating that encourages bone on-growth. In some instances, the transfixing implant is between 35 mm and 80 mm in length and between 7 mm and 13 mm in diameter. In some embodiments, the transfixing implant extends through a posterocranial region of the sacroiliac joint and the intra-articular implant extends posterocaudal to anterocranial within the sacroiliac joint. In some embodiments, the transfixing implant extends through a middle region of the sacroiliac joint and the intra-articular implant extends posterior to anterior within the sacroiliac joint. In other embodiments, the transfixing implant extends through a middle region of the sacroiliac joint and the intra-articular implant extends posterocaudal to anterocranial within the sacroiliac joint. In yet other embodiments, the transfixing implant extends through a posterocaudal region of the sacroiliac joint and the intra-articular implant extends posterocranial to anterocaudal within the sacroiliac joint.

In some instances, more than one transfixing implants are placed by repeating lateral approach steps for placing each transfixing implant. In some embodiments, a superior transfixing implant extends through a posterior region of the sacroiliac joint, an inferior transfixing implant extends through an anterior region of the sacroiliac joint, and the intra-articular implant extends posterocaudal to anterocranial within the sacroiliac joint, bisecting the superior and inferior transfixing implants. In other embodiments, a superior transfixing implant extends through a posterocranial region of the sacroiliac joint, an inferior transfixing implant extends through a posterocaudal region of the sacroiliac joint, and the intra-articular implant extends posterior to anterior within the sacroiliac joint, bisecting the superior and inferior transfixing implants. In yet other embodiments, a superior transfixing implant extends through a posterocranial region of the sacroiliac joint, an inferior transfixing implant extends through a posterocaudal region of the sacroiliac joint, and the intra-articular implant extends posterocaudal to anterocranial within the sacroiliac joint.

In some instances, more than one transfixing implants are placed by repeating lateral approach steps for placing each transfixing implant and more than one intra-articular implants are placed by repeating posterior approach steps for placement of each intra-articular implant. In some embodiments, a superior transfixing implant extends through a posterocranial region of the sacroiliac joint, an inferior transfixing implant extends through a posterocaudal region of the sacroiliac joint, a superior intra-articular implant extends posterocranial to anterocaudal within the sacroiliac joint, and an inferior intra-articular implant extends posterocaudal to anterocranial within the sacroiliac joint, the intra-articular implants converging at their distal ends.

In some instances, more than one intra-articular implants are placed by repeating posterior approach steps for placement of each intra-articular implant. In some embodiments, the transfixing implant extends through a posterior region of the sacroiliac joint, a superior intra-articular implant extends posterocranial to anterocaudal within the sacroiliac joint, and an inferior intra-articular implant ex-tends posterocaudal to anterocranial within the sacroiliac joint, the intra-articular implants converging at their distal ends and the transfixing implant located posterior to the converging distal ends.

According to another aspect of the present disclosure, there is provided a method of stabilizing a sacroiliac joint of a patient through a hybrid lateral-posterior approach. The method includes making a first incision for a posterior approach, the first incision located along a lateral border of a sacroiliac joint as viewed from an anterior-posterior view of a pelvic region of the patient in prone position. A first initial void is formed between the first incision and the sacroiliac joint. An intra-articular introducer is advanced through the first initial void and into the sacroiliac joint. A first intermediate void that is larger in diameter than the first initial void is formed by advancing at least one intra-articular dilator over the intra-articular introducer and into the sacroiliac joint. A first final void that expands the first intermediate void within the sacroiliac joint is then formed, the first final void having a sacroiliac joint extension depth appropriate for reception of an intra-articular implant. The intra-articular implant is then placed within the first final void so that the intra-articular implant extends into the sacroiliac joint.

The method further includes making a second incision for a lateral approach, the second incision located anterior to a posterior sacral wall and inferior to an ala as viewed from a lateral view of the pelvic region of the patient in prone position. A second initial void is formed between the second incision and a lateral aspect of an ilium. A lateral introducer is advanced through the second initial void, through the ilium, across the sacroiliac joint, and into a sacrum. A second intermediate void that is larger in diameter than the second initial void is formed by advancing at least one lateral dilator over the lateral introducer to the lateral aspect of the ilium. A second final void is formed, extending from the second intermediate void, through the ilium and sacroiliac joint, and into the sacrum. The second final void has a sacral extension depth appropriate for reception of a transfixing implant. The transfixing implant is then placed within the second final void so that the transfixing implant extends across the sacroiliac joint with its distal end within the sacrum and its proximal end flush with the lateral aspect of the ilium. As such, that the sacroiliac joint is stabilized by the transfixing implant and the intra-articular implant.

BRIEF DESCRIPTION OF DRAWINGS

The following detailed description of the present disclosure may be better understood, by way of example only, with reference to the following drawings. The elements of the drawings are not necessarily to scale relative to each other, emphasis being placed upon clearly illustrating the principles of the disclosure. Furthermore, like reference numerals designate corresponding features in several views or insets.

DETAILED DESCRIPTION

The present disclosure is directed to methods of stabilizing the sacroiliac joint when there is injury, pain, or trauma to the sacroiliac joint. The disclosed methods or procedures include positioning at least on transfixing implant across the sacroiliac joint and/or positioning at least one intra-articular implant within the sacroiliac joint intra-articular space. The methods are conducted so that the sacroiliac joint in stabilized with minimal or substantially no incidences of surgical complications or infection.

Figure 1:
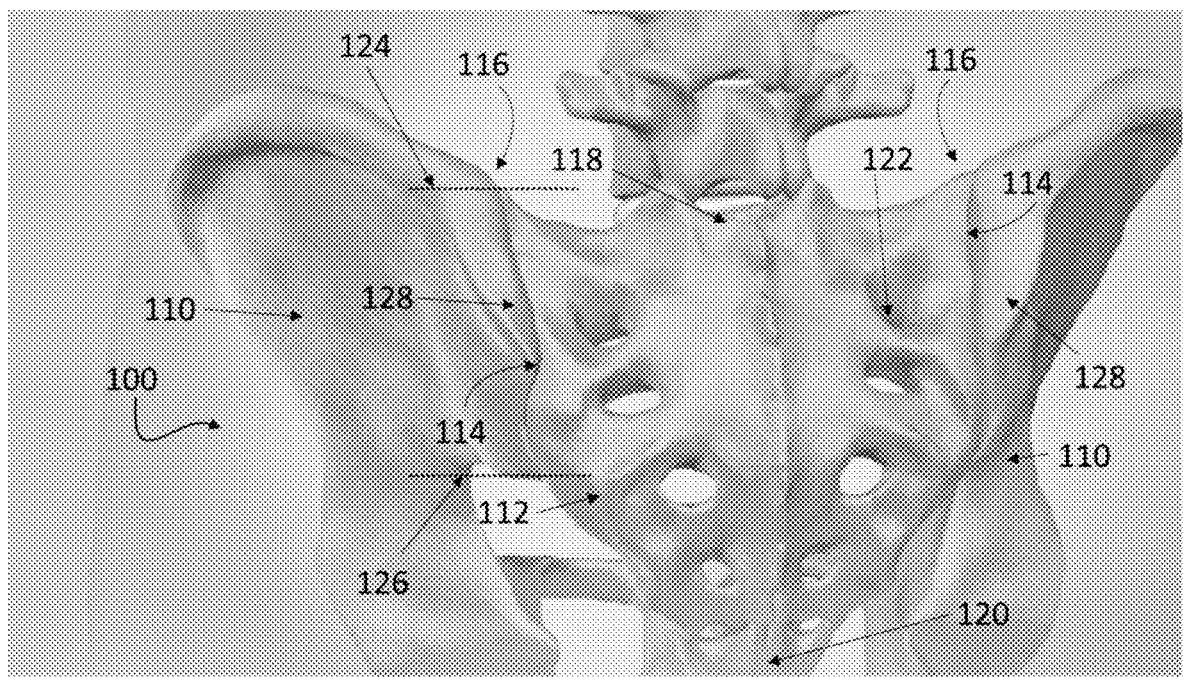
FIG. 1 is a perspective posterior view of a pelvic region including ilia, a sacrum, and sacroiliac joints for treatment with sacroiliac joint stabilization systems and methods of the present disclosure.
Figure 2:
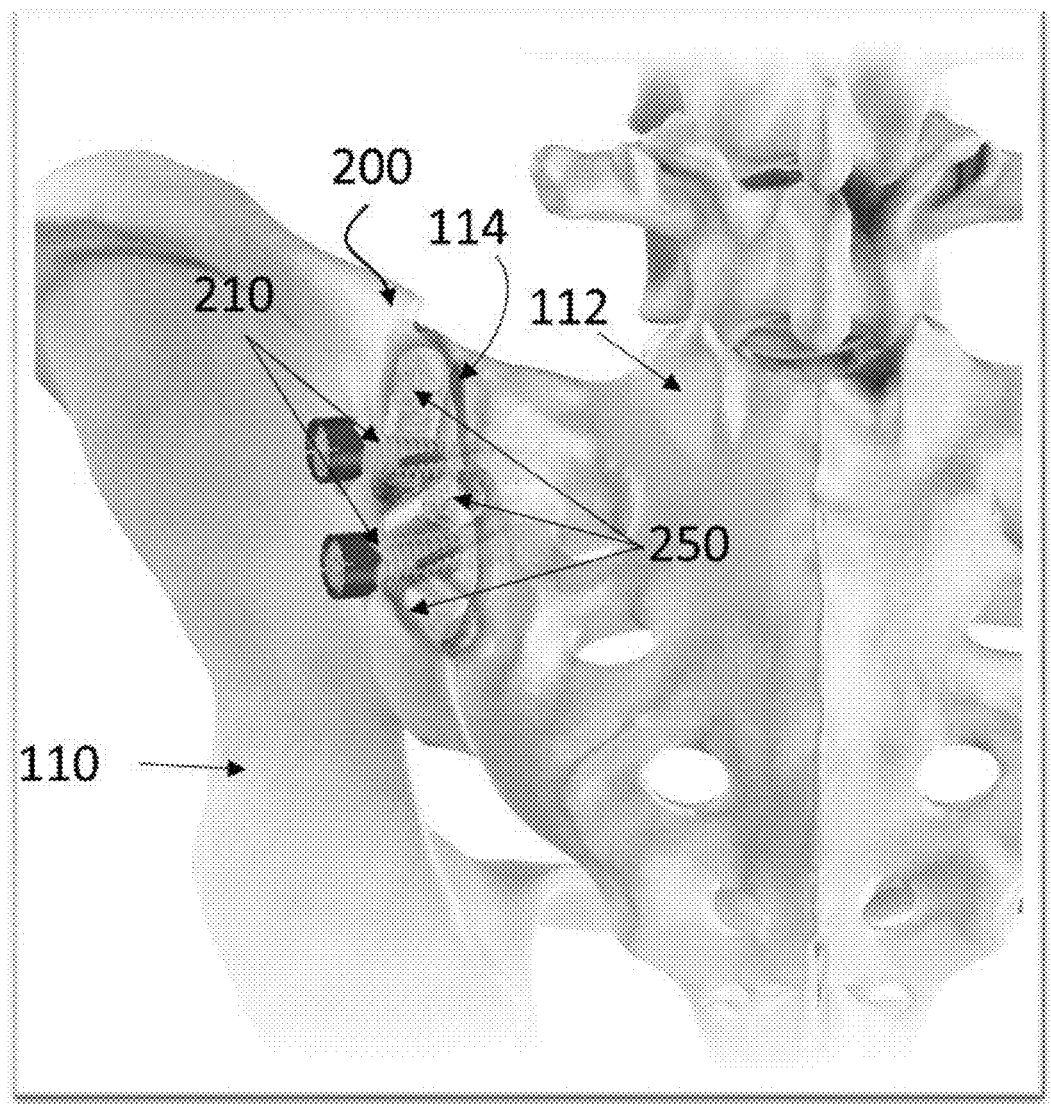
FIG. 2 is a perspective posterior view of the pelvic region with a sacroiliac joint stabilization system having transfixing implants and intra-articular implants administered to stabilize the sacroiliac joint according to methods of the present disclosure.
Figure 3:
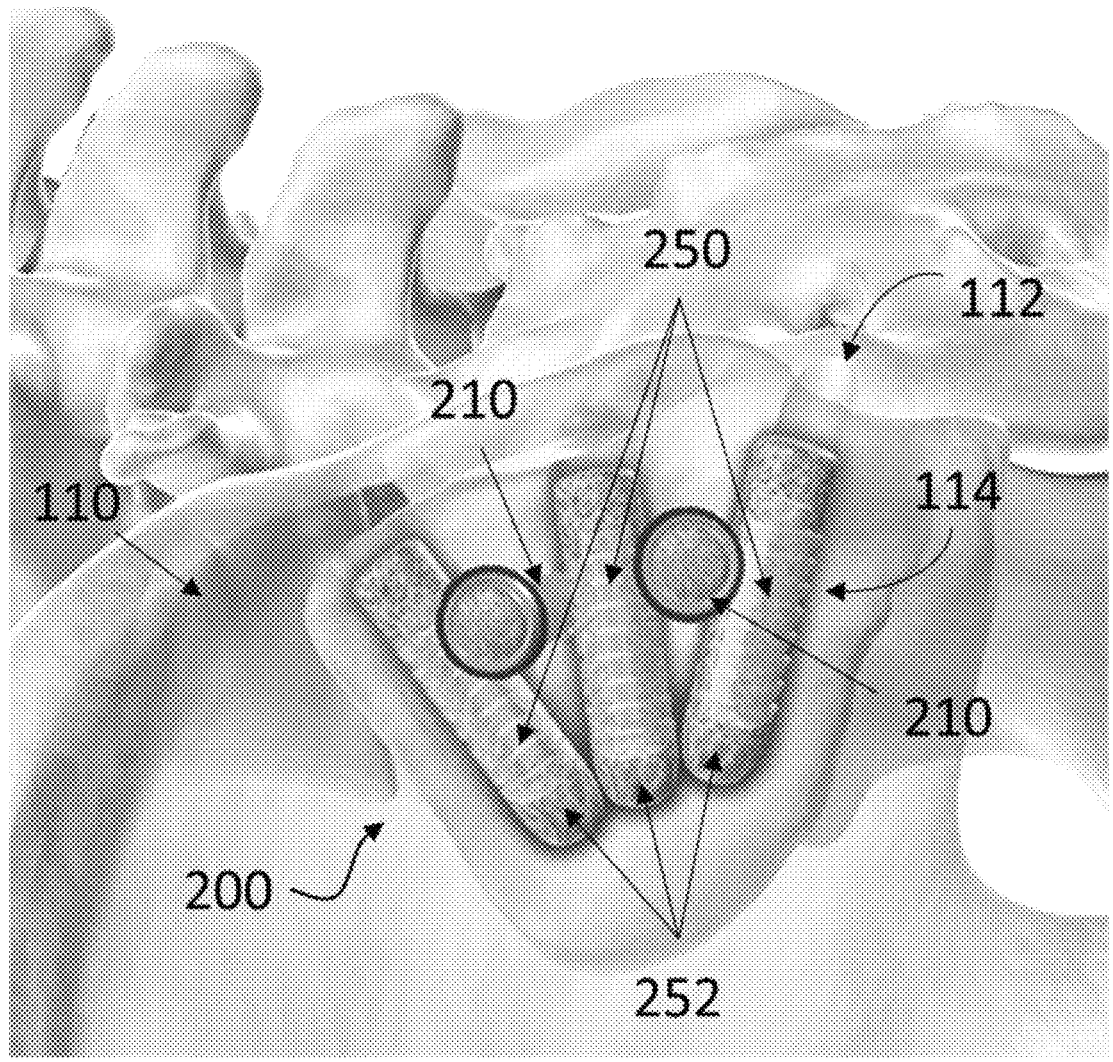
FIG. 3 is a perspective lateral view of the pelvic region with the sacroiliac joint stabilization system of FIG. 2.

FIG. 1 shows the pelvic region in which the sacroiliac joint system is to be placed, with said system shown in the pelvic region in FIG. 2 and FIG. 3. FIGS. 4 through 16 depict steps and components for placement of one or more transfixing implants across the sacroiliac joint. In FIGS. 17 through 26, steps and components for placement of one or more intra-articular implants within the sacroiliac joint are shown. In FIGS. 27 through 35, the target insertion zone of the pelvic region is shown for placement of one or more transfixing implants and/or intra-articular implants.

Referring to FIG. 1, there is depicted the pelvic region 100 of a person, where pelvic region 100 includes a sacrum 112, two ilia 110, and sacroiliac joints 114 formed between sacrum 112 and each ilia 110. Sacroiliac joint 114 is the joint between sacrum 112 and ilium 110 and involves connective ligaments that join sacrum 112 and ilium 110. Each sacroiliac joint 114 is a synovial plane joint that interlocks sacrum 112 and ilium 110 and has substantial similarity to the other sacroiliac joint 114 of the same person. However, sacroiliac joints 114 include irregularities and may vary between persons.

Sacrum 112 includes an apex 120 and a base 118, as well as alae 116 on either side of base 118. Base 118 is the broad region superior to apex 120 and assists in supporting the weight of the body. Each ala 116, or "wing", is a border of the pelvic brim and articulates with sacroiliac joint 114. Sacrum 112 includes a plurality of foramen on each of the anterior and posterior sacral surfaces that provide passage for sacral nerves. The S1 foramen 122 are superior to the remaining foramen. The posterior superior iliac spine (PSIS) 128 is located at the posterior border of each ala 116 and is separated by a notch from the posterior inferior iliac spine. Also shown in FIG. 1 is a superior joint border 124 of the sacroiliac joint 114 and an inferior joint border 126 of the sacroiliac joint 114. When there is injury or trauma or a disorder causing same to the sacroiliac joint 114, it is desirable to stabilize the joint for pain management.

As shown in FIG. 2, a sacroiliac joint stabilization system 200 is shown as located in pelvic region 100. Such system is implanted in defined locations according to the methods of the present disclosure. Sacroiliac joint stabilization system 200 includes at least one transfixing implant 210 and at least one intra-articular implant 250. Though two transfixing implants 210 and three intra-articular implants 250 are depicted in FIG. 2, more or less of each are possible for placement according to the disclosed methods. Likewise, implant locations are variable according to the methods of the present disclosure, as described in greater detail below. Transfixing implants 210 typically are positioned to enter or span sacroiliac joint 114 in a lateral direction, while intra-articular implants 250 typically enter sacroiliac joint 114 in its intra-articular space in a posterior-anterior direction. The placement steps for each implant are described below.

In FIG. 3, there is shown sacroiliac joint stabilization system 200 from a lateral view. Located about each implant are optional bone chips 252, which aid implant fixation and joint stabilization. Bone chips 525, if included, are deposited during the implant placement process as described below in detail. When present, bone chips 252 are optionally located below, above, or generally about some or all of transfixing implants 210 and intra-articular implants 250.

For hybrid approaches of implanting sacroiliac joint stabilization system 200, a combination of one or more transfixing implants 210 and/or intra-articular implants 250 are used. Placement order of each implant varies according to the method used, though transfixing implants 210 are often placed prior to intra-articular implants 250. However, in some embodiments, intra-articular implants 250 are implanted prior to transfixing implants 210, or the implantation of transfixing implants 210 and intra-articular implants 250 is alternated. In some instances, only transfixing implants 210 or only intra-articular implants 250 are used for sacroiliac joint stabilization system 200.

Figure 4:
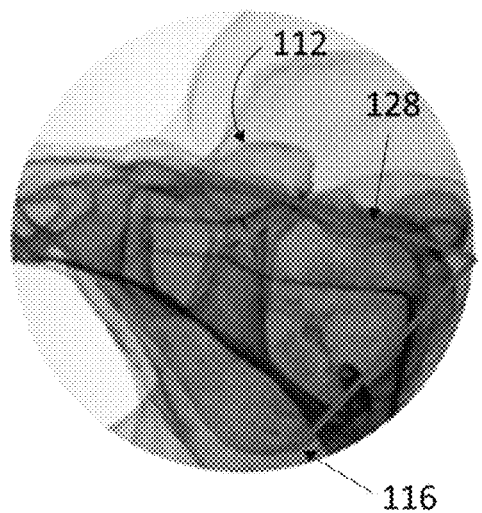
FIG. 4 is a perspective lateral view of the pelvic region with the posterior superior iliac spine (PSIS) and ala marked with lines to identify the surgical zone for placement of transfixing implants of the sacroiliac joint stabilization system of FIG. 2.

Now referring to FIG. 4, there is depicted an exemplary image showing an initial body positioning for insertion of at least one transfixing implant 210. For positioning, the patient is to lay prone on a flat surface that is at an appropriate height for imaging and marking. Exemplary surfaces are radiolucent tables. The patient may be draped according to the preference of medical personnel. The patient and surface are arranged such that the C-arm of the fluoroscopic imaging system is capable of free movement to reach inlet, outlet, and lateral views. Using fluoroscopy or another appropriate imaging technique known in the art, the alar lines are viewed. In a lateral view, fluoroscopy is positioned directly at sacrum 112 to allow viewing of alar lines, posterior and anterior sacral walls, and the endplate of S1 foramen 122. The C-arm is optionally moved side-to-side, or "wagged", to achieve a superimposed image of the alar lines and to define a "true lateral" view. From this view, ala 116 is marked with a skin line marker. From the same viewpoint, the PSIS 128 is located and marked with a skin line marker, with the line drawn until it connects with the marked alar line.

Figure 5:
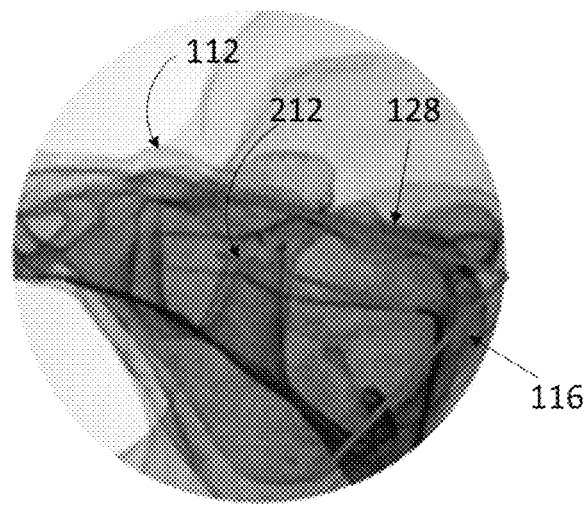
FIG. 5 is a perspective lateral view of the pelvic region with a lateral incision marker for placement of transfixing implants of the sacroiliac joint stabilization system of FIG. 2.

Next, in outlet view, fluoroscopy C-arm is positioned approximately 25 to 35 degrees cephalad to allow viewing of the sacral foramen in an open position. In this view, S1 foramen 112 is identified and lines lateral and parallel to PSIS 128 are marked. In FIG. 5, while back in the "true lateral" view, an approximately 1 to 3 cm incision 212 that is approximately 2 cm anterior to the posterior sacral wall and approximately 1 cm inferior to the alar line is made. However, the position and length of incision 212 may be varied depending on intended position, angle, and number of transfixing implants 210. Variations of this incision and positioning are discussed in detail below.

Figure 6:
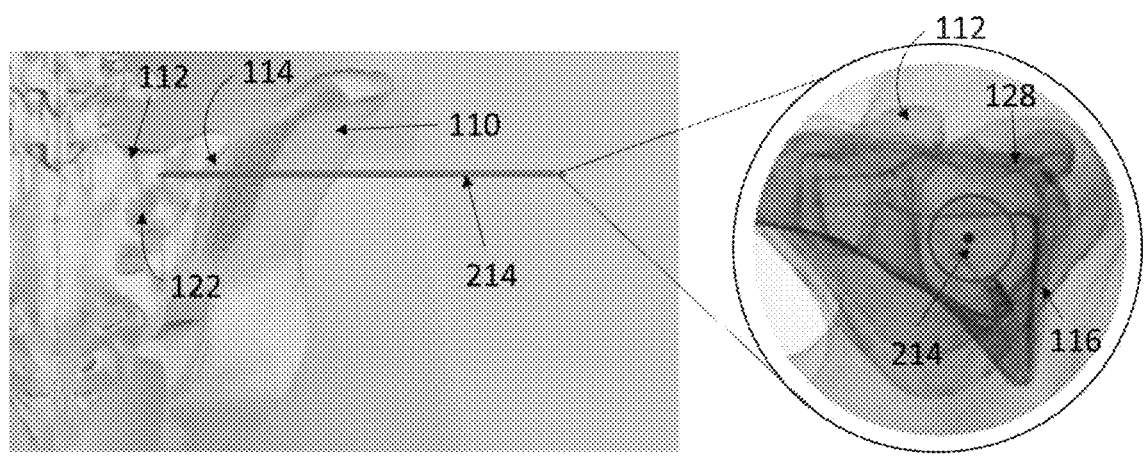
FIG. 6 is a perspective posterior view (left) and perspective lateral view (right) of the pelvic region with a lateral introducer for placement of transfixing implants of the sacroiliac joint stabilization system of FIG. 2.

After incision of skin and fascia, dissection to ilium 110 is undertaken. Next, as shown in FIG. 6, lateral introducer 214 is docked on the lateral aspect of ilium 110 at the level of S1 foramen 122. This position is approximately 2 cm anterior of the posterior sacral wall and approximately 1 cm inferior to the alar line. Lateral introducer 214 is, in some cases, a K-wire or Steinmann pin, or any other introducer known in the art. In some instances, lateral introducer 214 is a semi-blunt Steinmann pin, while in other instances it is a sharp Steinmann pin. When a Steinmann pin is used as lateral introducer 214, it may be a 2.4 mm or 3.2 mm diameter, 254 mm length Steinmann pin. While keeping lateral introducer 214 parallel to the floor, it is tapped into place using a mallet or other tapping instrument know in the art. In a preferred embodiment, lateral introducer 214 is tapped approximately 1 cm into place while angling toward the top of S1 foramen 122.

At this point, placement and position of lateral introducer 214 are optionally confirmed in the lateral view. Advancement into ilium 110 then continues to a point approximately 2 mm into ilium 110. Placement of lateral introducer 214 is further confirmed in outlet and inlet views prior to further advancement. In outlet view, fluoroscopy C-arm is positioned approximately 25 to 35 degrees cephalad to allow viewing of lateral introducer 214. In inlet view, fluoroscopy C-arm is positioned approximately 25 to 35 degrees caudal to allow viewing of same. Other views and angles are possible for confirming lateral introducer position and trajectory. After confirmation, lateral introducer 214 is advanced across sacroiliac joint 114 and into sacrum 112. The mallet or other tapping instrument is used to advance lateral introducer 214 to a desired depth.

Figure 7:
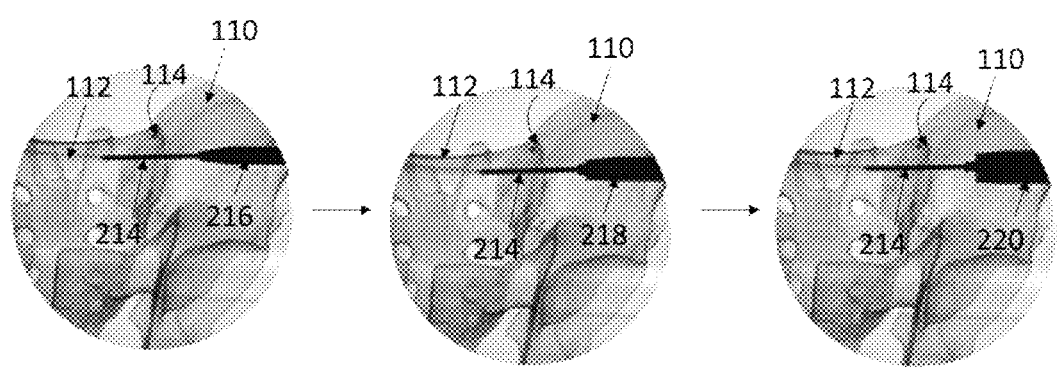
FIG. 7 are perspective posterior views of the pelvic region with a first dilator (left), second dilator (center), and third dilator (right) positioned over the lateral introducer for placement of transfixing implants of the sacroiliac joint stabilization system of FIG. 2.

As shown in the leftmost panel of FIG. 7, a first dilator 216 is then positioned over lateral introducer 214 and advanced until secure on the wall of ilium 110. The central panel of FIG. 7 shows the second dilator 218 positioned over first dilator 216 and lateral introducer 214 as it is advanced until secure on the wall of ilium 110. Finally, in the rightmost panel of FIG. 7, the third dilator 220 is positioned over second dilator 218, first dilator 216, and lateral introducer 214 and advanced and secured on the wall of ilium 110. This process enlarges the implant hole to accommodate drilling and implant placement. After third dilator 220 is inserted, both first dilator 216 and second dilator 218 are removed. The sizing of dilators is such that first dilator 216 fits over lateral introducer 214 and is smaller in diameter than second dilator 218, which is smaller in diameter than third dilator 220. At this point a dilator guide handle or other stability device is optionally attached to third dilator 220 for additional stability and handling.

Figure 8:
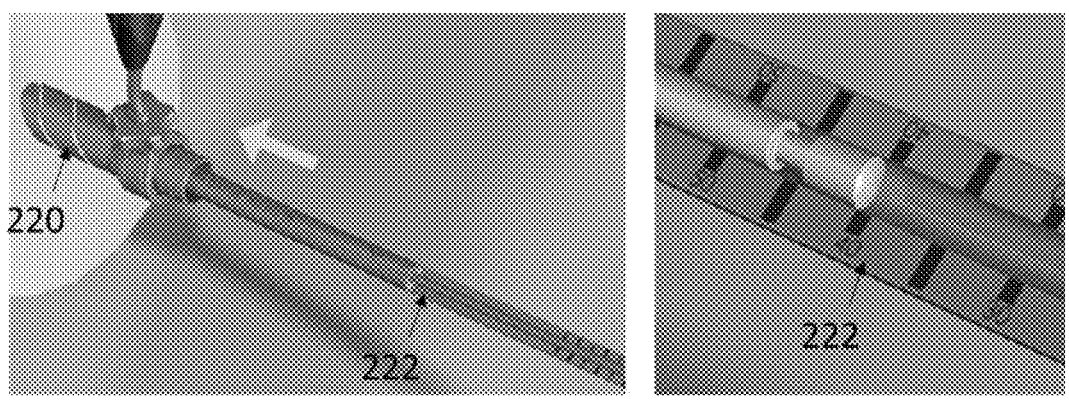
FIG. 8 is a perspective lateral view and inset view of the pelvic region with a pin depth gauge inserted inside the third dilator for placement of transfixing implants of the sacroiliac joint stabilization system of FIG. 2.

Referring now to FIG. 8, implant sizing and drilling depth are determined using a pin depth gauge 222. This pin depth gauge 222 is placed over lateral introducer 214 and inside third dilator 222. It is then advanced until secure on the wall of ilium 110. From this position, markings on pin depth gauge 222 are read to determine the appropriate implant length. For transfixing implants 210, lengths range from approximately 35 mm to 80 mm. Transfixing implant lengths of approximately 35 mm, 40 mm, 45 mm, 50 mm, 55 mm, 60 mm, 65 mm, 70 mm, 75 mm, 80 mm, or intervening lengths are possible. Transfixing implant 210 has a diameter ranging from approximately 7 mm to 13 mm. In some embodiments, transfixing implant 210 ranges from 40 mm to 80 mm in length and 7 mm to 13 mm in diameter. In other embodiments, transfixing implant 210 ranges from 35 mm to 60 mm in length and 9.5 mm to 11 mm in diameter.

Figure 9:
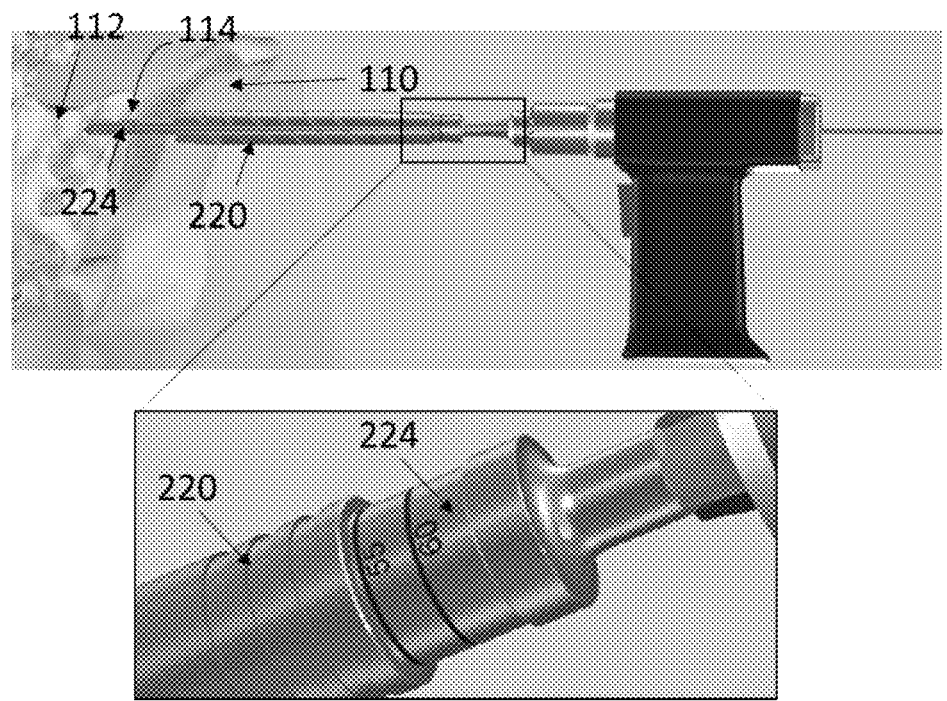
FIG. 9 is a perspective posterior view and inset view of the pelvic region with a lateral drill bit inserted inside the third dilator for placement of transfixing implants of the sacroiliac joint stabilization system of FIG. 2.

As shown in FIG. 9, drilling occurs to enlarge the implant hole through ilium 110, sacroiliac joint 114, and into sacrum 112. The desired lateral drill bit 224 is attached to the drill power unit. When appropriate, the power unit utilizes a Jacobs's adaptor. The size of lateral drill bit 224 is determined to accommodate transfixing implant 210 with a desired length and diameter. For instance, a 9.5 mm or 11 mm lateral drill bit 224 is used to drill a hole for a 9.5 mm or 11 mm diameter transfixing implant 210, respectively. Lateral drill bit 224 is, in some instances, cannulated.

Lateral drill bit 224 is inserted over lateral introducer 214 and over third dilator 220, and is positioned parallel to the floor for drilling. Advancement of lateral drill bit 224 across sacroiliac joint 114 and into sacrum 112 is performed slowly. After advancement is complete, a blocking pin is inserted into a rear portion of the drill power unit until flush with lateral introducer 214 and held into place as drill power unit is removed. Before lateral drill bit 224 is removed, it may be optionally used, along with third dilator 220, to confirm implant length. Markings on lateral drill bit 224 indicate drilling depth, as shown in the inset of FIG. 9.

Figure 10:
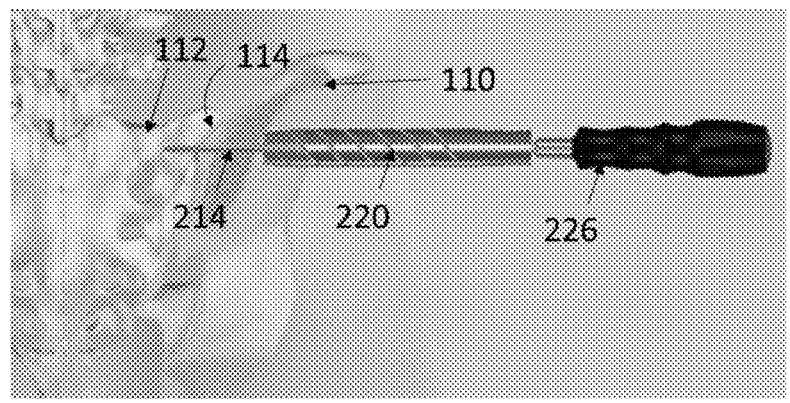
FIG. 10 is a perspective posterior view of the pelvic region with a lateral decortication instrument inserted inside the third dilator for placement of transfixing implants of the sacroiliac joint stabilization system of FIG. 2.

Now referring to FIG. 10, when drilling is complete, the drill is removed and a lateral decortication instrument 226 is used to decorticate sacroiliac joint 114. Lateral decortication instrument 226 is inserted into third dilator 220 and advanced until inside sacroiliac joint 114. Once in position, lateral decortication instrument 226 is rotated slowly to decorticate the joint. After decortication is complete, lateral decortication instrument 226 is removed from third dilator 220.

At this point, the appropriately-sized transfixing implant 210 is ready for insertion. As described above, transfixing implant lengths and diameters vary according to intended application and position. The selected size of transfixing implant 210 further depends on the number of transfixing implants 210 and, optionally, intra-articular implants 250 to be used. The intended locations of each implant of sacroiliac joint stabilization system 200 further determine the appropriate size of transfixing implants 210. In some instances, each transfixing implant 210 is the same size, while in other instances where more than one transfixing implant 210 is used, implant lengths and/or diameters differ. Transfixing implants 210 are typically composed of a surgically-compatible material, such as titanium. Optionally, transfixing implants 210 include a pro-growth coating, such as HA$^{nano}$ Surface® (Promimic, Warsaw, IN), described in greater detail below regarding intra-articular implants 250.

Figure 11:
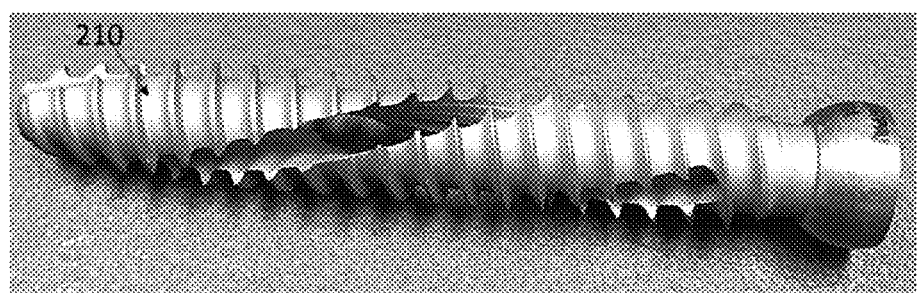
FIG. 11 is a perspective view of a first embodiment of a transfixing implant of the sacroiliac joint stabilization system of FIG. 2.

An exemplary transfixing implant 210 is depicted in FIG. 11, where the screw body of transfixing implant 210 is generally of a uniform outer diameter and outer helical diameter, with exceptions at the screw head and tapered insertion point. In the depicted embodiment, transfixing implant 210 includes an inner channel with windows into a helical channel for removal of bone as it is inserted. Such an exemplary transfixing implant 210 is described in U.S. Pat. No. 11,607,256 for "Bone Screw and Method of Using Same."

Figure 12:
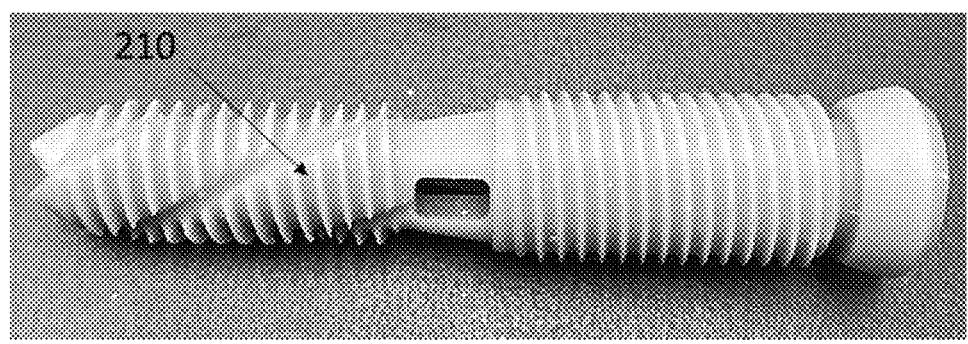
FIG. 12 is a perspective view of a second embodiment of a transfixing implant of the sacroiliac joint stabilization system of FIG. 2.

A second embodiment of an exemplary transfixing implant 210 is shown in FIG. 12, where the screw body is of variable outer diameters and outer helical diameters. Similar to the embodiment in FIG. 11, the second embodiment in FIG. 12 includes an inner channel with windows into a helical channel for removal of bone as it is inserted. This exemplary transfixing implant 210 is described in U.S. Non-Provisional patent application Ser. No. 17/892,373 and U.S. Non-Provisional patent application Ser. No. 17/017,403, the contents of which are incorporated in their entirety by reference. Transfixing implant 210 is, in general, a fully threaded and cannulated screw with double helix threads configured to be inserted into pre-drilled bone. Transfixing implant 210 optionally includes a load distribution cap, as shown below.

In some instances, transfixing implant 210 is self-drilling and/or self-decorticating. In such cases, transfixing implant 210 is inserted without the drilling and/or decortication steps described above that are undertaken with separate instruments. Using a pilot hole provided by lateral introducer 214 and dilators, such a screw may be directly advanced into the desired location where the distal screw resides within sacrum 112 and the screw body crosses sacroiliac joint 114.

Figure 13:
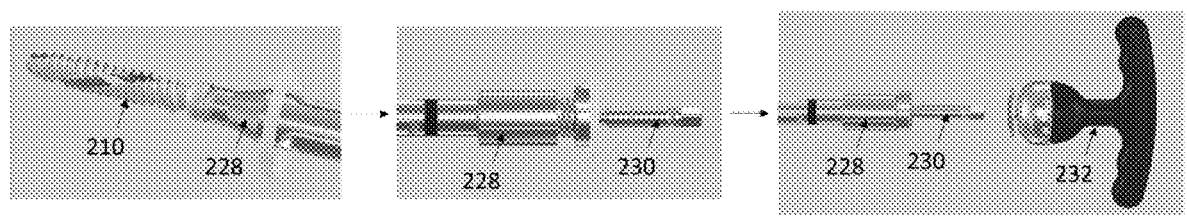
FIG. 13 are a perspective views of an inserter system for placement of a transfixing implant of the sacroiliac joint stabilization system of FIG. 2.

Now referring to FIG. 13, transfixing implant 210 is threaded at its head onto an inserter outer sleeve 228 by rotating inserter outer sleeve 228 until transfixing implant 210 is secure (leftmost panel). Next, inserter inner shaft 230 is inserted inside inserter outer sleeve 228 with its hex seated in the screw head of transfixing implant 210. The sizes of inserter inner shaft 230 and inserter outer sleeve 228 are such that inserter outer sleeve 228 receives inserter inner shaft 230 therewithin. When screw head of transfixing implant 210 is not hex-receptive, an appropriately shaped inserter inner shaft 230 is used such that it may be received within the screw head.

Inserter inner shaft 230 is locked once it is seated in the screw head of transfixing implant 210 (center panel of FIG. 13). The locking is performed by rotating the knob of inserter inner shaft 230 clockwise. At this point, a handle 232, such as a ratcheting T-handle, is attached to inserter inner shaft 230 (rightmost panel of FIG. 13).

Figure 14:
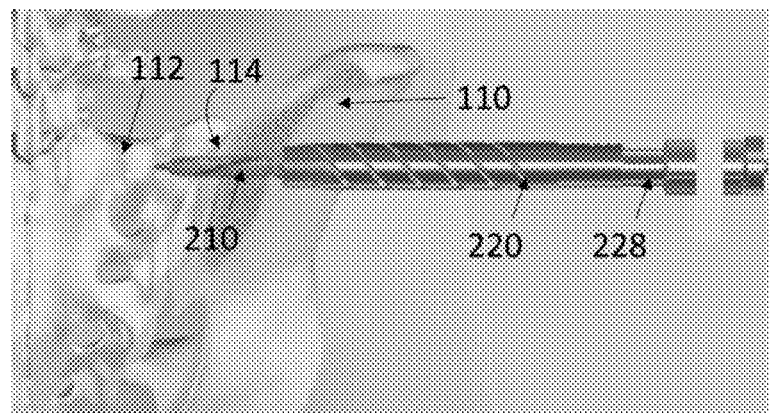
FIG. 14 is a perspective posterior view of the pelvic region with the inserter outer sleeve inserted inside the third dilator for placement of transfixing implants of the sacroiliac joint stabilization system of FIG. 2.

The assembly with transfixing implant 210 shown in FIG. 13 is then placed over lateral introducer 214, as shown in FIG. 14. Transfixing implant 210 is advanced by rotation in a clockwise direction to reach the desired depth of the implant. This advancement occurs through ilium 110, across sacroiliac joint 114, and into sacrum 112 until the proximal end of transfixing implant 210 is flush with the lateral edge of ilium 110.

Following insertion, the instruments are to be removed. For removal, the blocking pin is reinserted into the rear of the drill power unit until flush with lateral introducer 214. Handle 232 is then placed into a neutral position, following which the knob of inserter inner shaft 230 is rotated counterclockwise for removal. Next, inserter outer sleeve 228 is rotated counterclockwise until it disengages with transfixing implant 210 and may be removed. Third dilator 220 is then removed, as well. After all other instruments are removed from the insertion site and no further transfixing implants 210 are to be inserted, lateral introducer 214 is removed. However, when further transfixing implants 210 are to be inserted, lateral introducer 214 is optionally left in position to determine spacing of other transfixing implants 210 using a fixed pin guide or other spacing instrument. Spacing of subsequent transfixing implants 210 is performed according to the desired application, number of implants, and position of other implants of sacroiliac joint stabilization system 200. The process for insertion of other transfixing implants 210 follows the same steps shown and described by FIG. 6 through FIG. 14, though locations differ.

For example, a pin guide might be a 14 mm or 16 mm fixed pin guide that is inserted over lateral introducer 214. The fixed pin guide is rotated to align it with the desired location of the next transfixing implant 210. At this location, a second lateral introducer may be advanced through the longer tube of the fixed pin guide for insertion, as shown in FIG. 6. The location of the next lateral introducer 214 is determined using outlet and/or inlet views of the fluoroscopy C-arm, as described above for the first lateral introducer placement.

Figure 15:
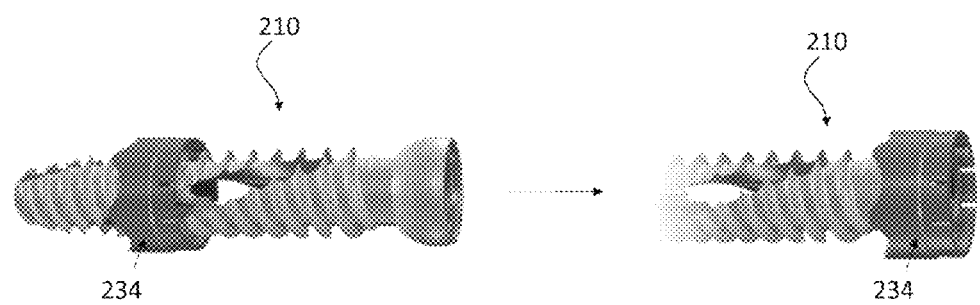
FIG. 15 is a perspective view of the sacroiliac joint stabilization system of FIG. 2 with a loading cap.

In some instances, a load distribution cap is placed on the proximal head of transfixing implant 210, as shown in FIG. 15. The size of cap should align with the diameter of transfixing implant 210. For example, a 9.5 mm loading cap would be used with a 9.5 mm diameter transfixing implant 210. For attachment, the loading cap is slid from the distal tip toward the head of transfixing implant 210. Serrated edge of the loading cap should face the distal tip, and the cap should be advanced until it fully covers the head of transfixing implant 210.

Transfixing implant 210 is removable, if desired. For removal, a lateral view using fluoroscopy should be utilized. After identification of transfixing implant 210, an approximately 1-2 cm incision is made in the desired location for removal. Lateral introducer 214 is inserted through the incision and into the center of transfixing implant 210. Next, first dilator 216, second dilator 218, and then third dilator 220 are sequentially placed over lateral introducer 214 until secure on ilium 110. All dilators but third dilator 220 are removed, and inserter outer sleeve 228 is placed over lateral introducer 214 and rotated until engaged with transfixing implant 210. Inserter inner shaft 230 is then placed inside inserter outer sleeve 228 with its hex aligned with and seated within the head of transfixing implant 210. Inserter inner shaft 230 is locked and handle 232 is set to reverse ratcheting position to rotate counterclockwise and remove transfixing implant 210.

Figure 16:
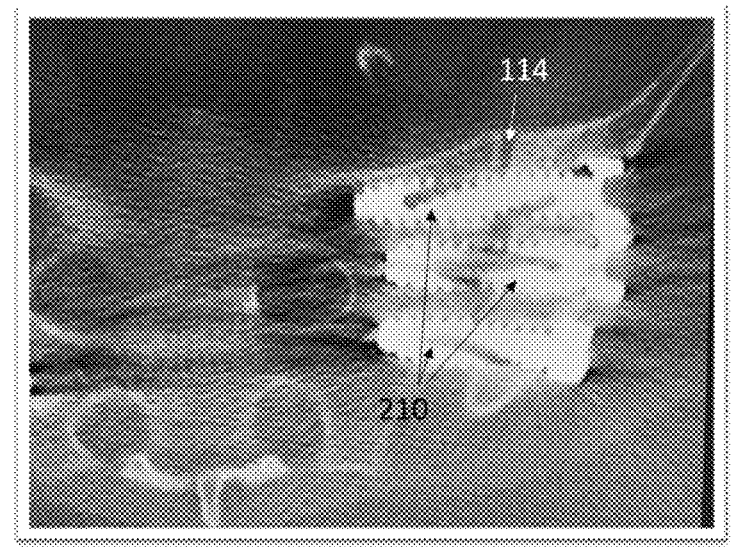
FIG. 16 is a perspective posterior view of the pelvic region with transfixing implants of the sacroiliac joint stabilization system of FIG. 2 positioned across the sacroiliac joint.

The placement of several transfixing implants 210 is shown in FIG. 16, with each spanning sacroiliac joint 114. Implants in FIG. 16 are similar to those shown in FIG. 11. Following placement of the one or more transfixing implants 210, one or more intra-articular implants 250 are to be inserted, if desired.

Figure 17:
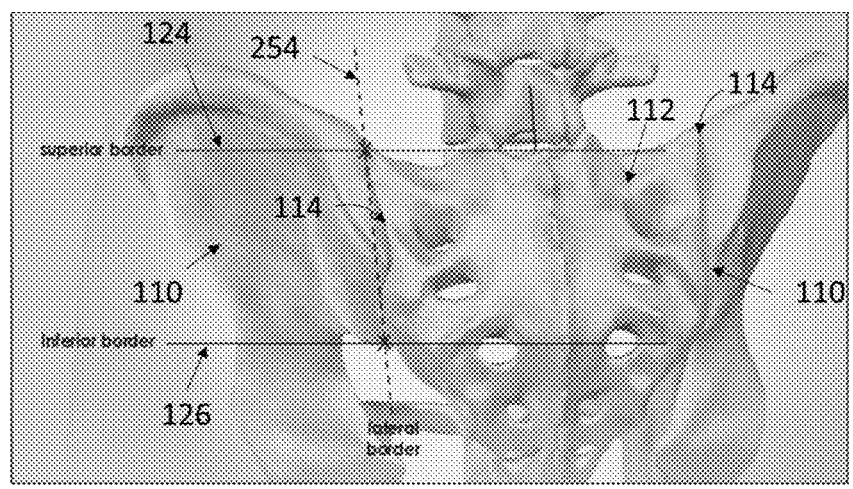
FIG. 17 is a perspective posterior view of the pelvic region with the superior joint border, inferior joint border, and lateral border marked to identify the surgical zone for placement of intra-articular implants of the sacroiliac joint stabilization system of FIG. 2.

Now referring to FIG. 17, there is shown a marking and locating region of the patient for insertion of one or more intra-articular implant 250. The aim of the intra-articular implant placement is to fix and fuse sacroiliac joint 114 which providing precision, safety, and control. For marking of the surgical area, the patient is placed in a prone position on an elevated surface, such as a radiolucent table or similar. Draping is performed according to the desires of medical personnel. The free movement of the fluoroscopy C-arm should be assessed prior to imaging and marking of the patient. Specifically, the C-arm is placed in a position or positions to determine sacroiliac joint boundaries, and especially superior joint border 124 and inferior joint border 126.

From anterior-posterior outlet and inlet views, as needed, the C-arm is tilted approximately 15 to 25 degrees oblique until the superior pubis border overlaps with the level of the S2 foramen. From this view, the vertical extent of sacroiliac joint 114 is visible, and superior joint border 124 and inferior joint border 126 may be established. Under this fluoroscopy imaging guidance, a guide pin is placed at the inter-alar line and a line is drawn to mark superior joint border 124 of the surgical zone. Similarly, a line is drawn to mark inferior joint border 126 of the surgical zone. Next, a lateral border 254 of sacroiliac joint 114 is identified, and intersections of lateral border 254 with superior joint border 124 and inferior joint border 126 are marked with an "X" or similar marking.

Figure 18:
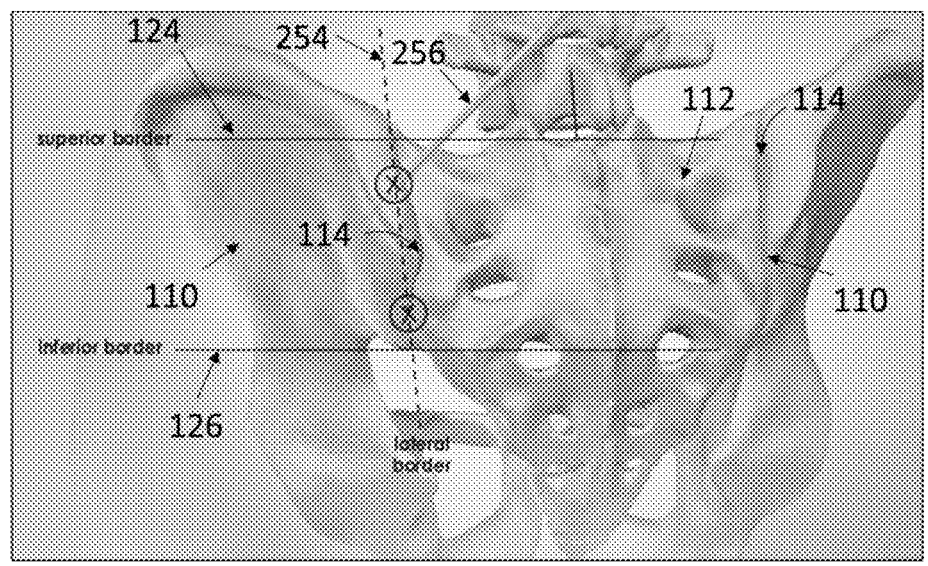
FIG. 18 is a perspective posterior view of the pelvic region with an intra-articular introducer for placement of intra-articular implants of the sacroiliac joint stabilization system of FIG. 2.

As shown in FIG. 18, a surgical incision is to be made along the lateral border region, where the incision is approximately 1-4 cm in length for the placement of two intra-articular implants 250. However, for the placement of one intra-articular implant 250, the incision would be short, such as approximately 1.5 cm. Similarly, for more than two intra-articular implants 250, a longer incision may be made. In the depicted example, the superior of the intra-articular implants 250 is to be placed approximately 2 cm inferior to superior joint border 124, as denoted in FIG. 18 by the upper "X" within a circle. The inferior of the intra-articular implants 250 is to be placed approximately 1.5-2 cm superior to inferior joint border 126, as denoted in FIG. 18 by the lower "X" within a circle. The position and length of the incision may be varied depending on intended position, angle, and number of intra-articular implants 250. Variations of this incision and positioning are discussed in detail below.

An optional arthrogram of sacroiliac joint 114 may be performed at this point to identify margins for introducer placement and drilling. For this technique, the fluoroscopy C-arm is placed in an oblique outlet view and a 22 #spinal needle is inserted into sacroiliac joint 114 to inject contrast. For example, 2 mL of contrast material is injected, though other amounts are possible such that sacroiliac joint 114 or relevant portions thereof are visible.

Referring back to FIG. 18, dissection anteriorly to sacroiliac joint 114 is performed. While in oblique outlet fluoroscopy view, an intra-articular introducer 256 is inserted in the direction of the superior marked circle and aligned with the angulation of sacroiliac joint 114. Intra-articular introducer 256 is, in some instances, a Steinmann pin, such as a 2.4 or 3.2 mm diameter, 254 mm length pin that is threaded and semi-blunt. However, other Steinmann pins or introducers are possible. An inlet view is then used at approximately 15 to 25 degrees oblique inlet caudal to assist with introducer alignment with sacroiliac joint 114. Finally, a true lateral view is used to visualize the slope of ala 116 and improve the angulation of intra-articular introducer 256 most inferiorly. A mallet or other impact instrument is used to tap intra-articular introducer 256 for advancement.

Figure 19:
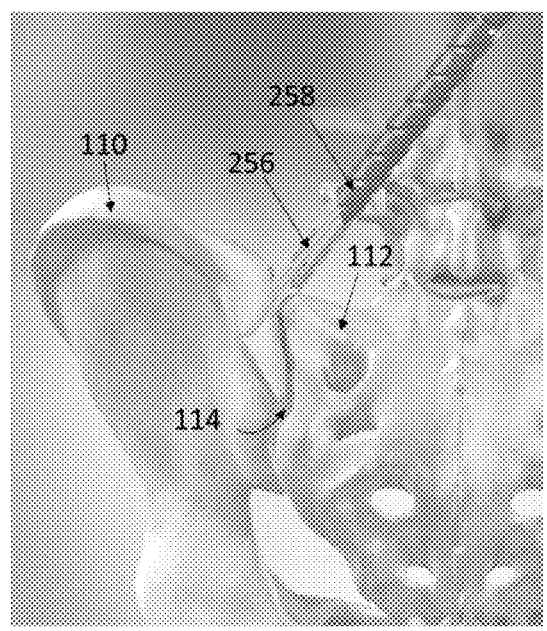
FIG. 19 is a perspective posterior view of the pelvic region with an inner dilator placed over the intra-articular introducer for placement of intra-articular implants of the sacroiliac joint stabilization system of FIG. 2.

Now referring to FIG. 19, incisions are made through the posterior sacral ligament immediately above and below intra-articular introducer 256 to allow an inner dilator 258, outer dilator 260, intra-articular drill bit 262, and intra-articular decortication instrument 264, respectively, to advance. Inner dilator 258 is then placed over intra-articular introducer 256 and advanced to the posterior edge of sacrum 112. Alignment and placement is confirmed by placing fluoroscopy C-arm in an anterior-posterior inlet view oriented approximately 15 to 25 degrees oblique inlet caudal. After verification, inner dilator 258 is advanced into sacroiliac joint 114 using a mallet or other tapping instrument.

Figure 20:
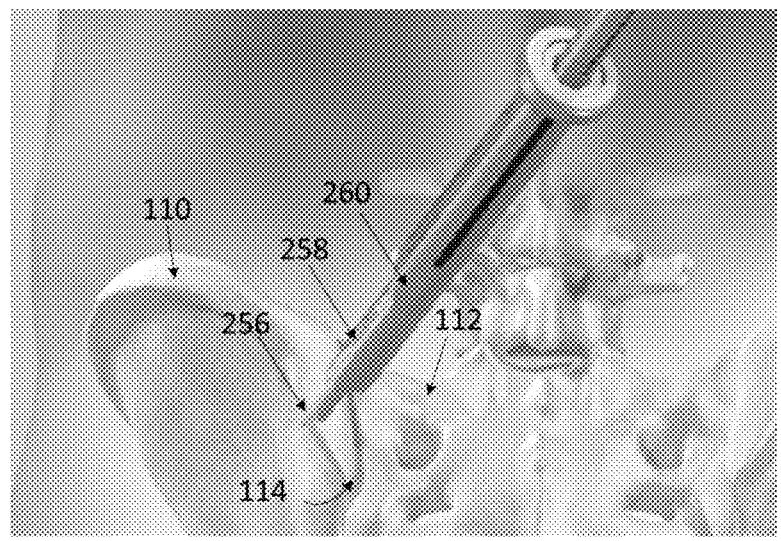
FIG. 20 is a perspective posterior view of the pelvic region with the inner dilator and an outer dilator placed over the intra-articular introducer for placement of intra-articular implants of the sacroiliac joint stabilization system of FIG. 2.

In FIG. 20, outer dilator 260 is inserted over inner dilator 258 with drill guide handles in the same direction as sacroiliac joint 114. Outer dilator 260 is advanced until it meets the posterior edge of sacrum 112. A mallet or other tapping instrument is used to tap outer dilator 260 into sacroiliac joint 114. Verification of outer dilator 260 trajectory and position may be performed by placing fluoroscopy C-arm in an anterior-posterior inlet view oriented approximately 15 to 25 degrees oblique inlet caudal.

Figure 21:
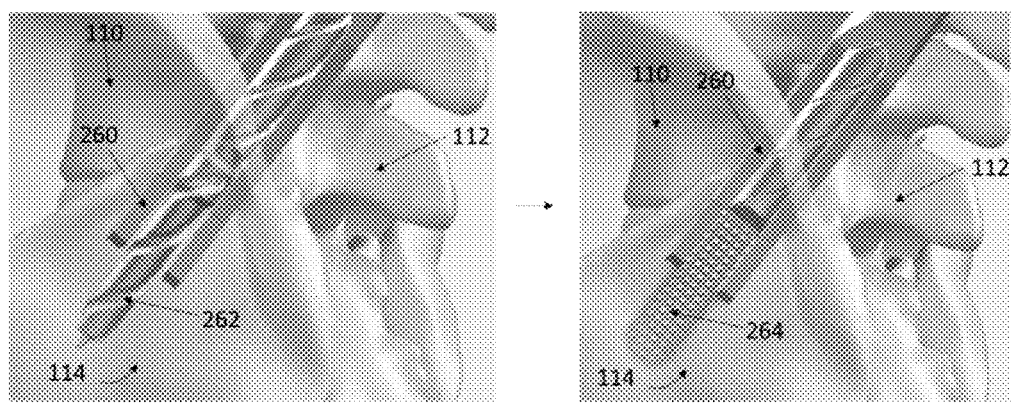
FIG. 21 are a perspective lateral views of the pelvic region with an intra-articular drill bit (left) and an intra-articular decortication instrument (right) within the outer dilator for placement of intra-articular implants of the sacroiliac joint stabilization system of FIG. 2.

In FIG. 21, inner dilator 258 and intra-articular introducer 258 have been removed to allow for placement of intra-articular drill bit 262 (left panel) and intra-articular decortication instrument 264 (right panel), respectively. A slap hammer or similar instrument is used to assist in removal of inner dilator 258 and intra-articular introducer 256 as necessary. For better viewing, the C-arm of the fluoroscope is placed in a true lateral orientation to check the angulation of outer dilator 260 toward sacroiliac joint space.

Next, the intra-articular drill bit 262 is attached to a ratcheting T-handle and positioned inside outer dilator 260. Intra-articular drill bit 262 is sized according to desired implant size. For instance, a 9 mm diameter intra-articular implant 250 would use a 9 mm intra-articular drill bit 262. Smaller or larger diameter intra-articular implants 250 would require smaller or larger intra-articular drill bits 262, respectively. While viewing in a true lateral view, intra-articular drill bit 262 is used to drill downward, with care to not cross the margins of sacroiliac joint 114. Afterwards, intra-articular drill bit 262 is removed from outer dilator 260 and bone chips 252 from drilling are optionally saved for bone grafting.

Next, intra-articular decortication instrument 264 is placed within outer dilator 260 to remove cartilage rostral and caudal to outer dilator 260. Intra-articular decortication instrument 264 is in some instances a decortication rasp, though other decortication instruments are possible.

If bone chips 252 or biologics are desired for insertion into the decorticated area, they are held in a sterile container until use. Bone chips 252 are prepared for insertion. For instance, bone chips 252 at a volume of approximately 1.7 cc's are prepared as a mixture of demineralized bone and autologous bone that was previously harvested, as described above. A funnel is used to direct bone chips 252 through outer dilator 260 and into the decorticated area. A bone tamp or other pressing instrument may be further used to press and position bone chips 252 in the correct location.

Figure 22:
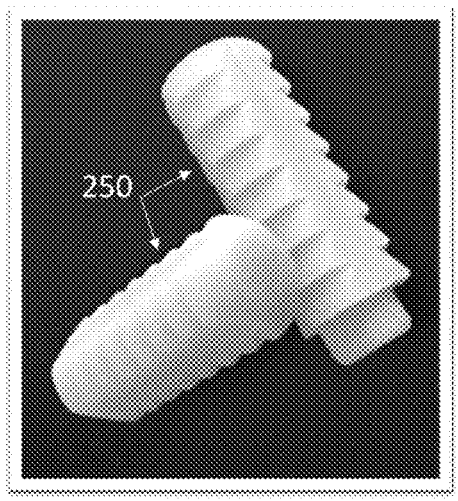
FIG. 22 is a perspective view of a first embodiment of intra-articular implants of the sacroiliac joint stabilization system of FIG. 2.

Now referring to FIG. 22, an exemplary first embodiment intra-articular implant 250 is shown. Intra-articular implant 250 is, for instance, machined from dense cortical bone with a cortical layer on each end. In some cases, intra-articular implant 250 is approximately 9 mm in diameter and 25 mm in length, and is packaged and stored in a sterile manner prior to insertion. However, other implant diameters and lengths are possible. Other features of intra-articular implant 250 include anti-mitigation teeth for resisting graft dislocation, a bullet-shaped nose for aiding in placement, and a proximal end extrusion for facilitating engagement with an inserter 266. This exemplary intra-articular implant 250 is described in U.S. Pat. No. D816,843.

Figure 23:
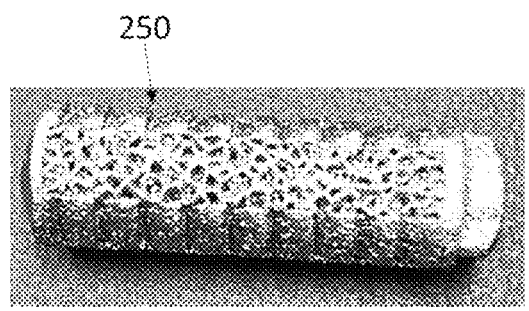
FIG. 23 is a perspective view of a second embodiment of an intra-articular implant of the sacroiliac joint stabilization system of FIG. 2.

In FIG. 23, an exemplary second embodiment intra-articular implant 250 is shown. This intra-articular implant 250 is 3D-printed has features such as anti-migration teeth for avoidance of undesired movement, a rounded nose for ease of placement, a central channel for integration, a pro-growth coating, and a plurality of porous regions to aid in integration after placement. The optional pro-growth coating is commercially-available and typically a wettable coating with optimized surface chemistry and nanoscale texture or features. Exemplary pro-growth coatings include HA$^{nano}$ Surface® (Promimic, Warsaw, IN), though other such coatings are possible such that they are compatible with implant materials and promote bone on-growth within target surgical zone 130. Porous regions have a network of micron-sized pores ranging from approximately 200 μm to 600 μm, such as 600 μm sized pores. However, other pore sizes are possible. The pores of the intra-articular implant 250 of FIG. 23 are shown as being irregularly shaped and spaced, though pore shape and organization is adjustable based on desired application. The coating is used to promote on-growth of bone, pores are utilized to promote ingrowth of bone, and cannulations of the implant are used to promote through-growth of bone. The material of the depicted intra-articular implant 250 is titanium with a nanoscale hydroxyapatite coating that allows for bone integration with the implant. However, other materials and coatings are possible. The implant length is approximately 26 mm or 31 mm, though other lengths are possible. The implant diameter is approximately 9 mm or 10.5 mm, respectively, though other diameters are possible.

Figure 24:
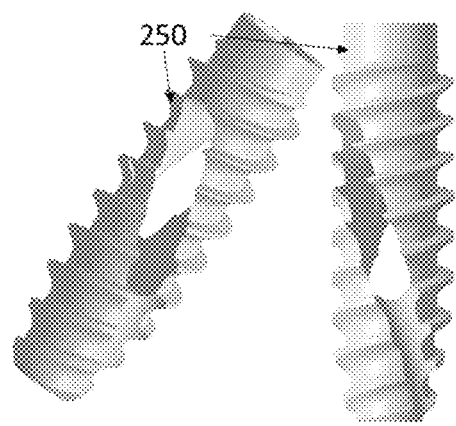
FIG. 24 is a perspective view of a third embodiment of an intra-articular implant of the sacroiliac joint stabilization system of FIG. 2.

In FIG. 24, there is depicted an exemplary third embodiment intra-articular implant 250. The third embodiment is a headless screw that decorticates as it advances down sacroiliac joint 114. The implant is a titanium intra-articular implant that is aggressively threaded with cutouts for movement of bone pieces as the implant advances through bone. Further, a central channel is available for storage of bone pieces as intra-articular implant 250 advances, the bone chips aiding in bone in-growth and implant integration following placement. Implant lengths and diameters vary according to application and may range from approximately 25 mm to 35 mm in length and approximately 9 mm to 11 mm in diameter.

Figure 25:
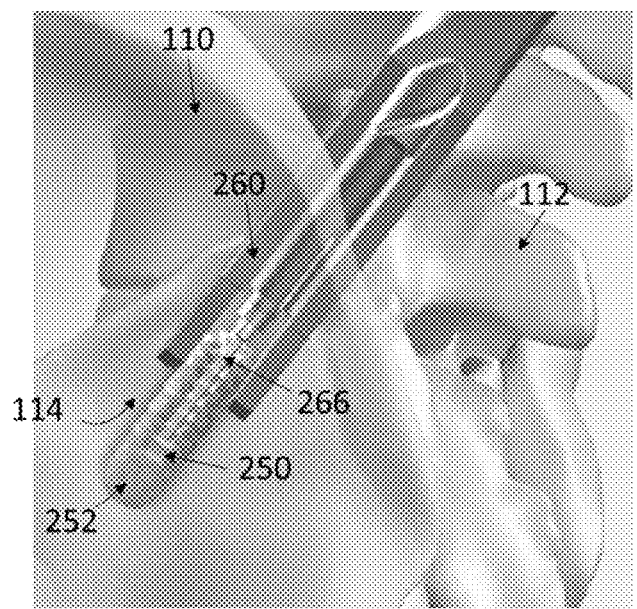
FIG. 25 is a perspective lateral view of the pelvic region with an intra-articular implant of the sacroiliac joint stabilization system of FIG. 2 being inserted in the sacroiliac joint, along with placement of bone chips about the implant.

Now referring to FIG. 25, after decortication and optional bone chip insertion, intra-articular implant 250 is ready for insertion. Intra-articular implant 250 is placed on inserter 266 using forceps or other sterile placement instrument. Inserter 266 and intra-articular implant 250 are placed through outer dilator 260 to guide intra-articular implant 250 into position. For visibility, inserter 266 optionally includes a removable titanium marking pin that is viewable via fluoroscopy. Once in correct position, a bone tamp or other instrument is used to push intra-articular implant 250 into any osteotomy. Further, a mallet or other tapping instrument may be used. After intra-articular implant 250 reaches the desired depth, which may be established via a stop on the bone tamp, inserter 266 and outer dilator 260 are removed.

Figure 26:
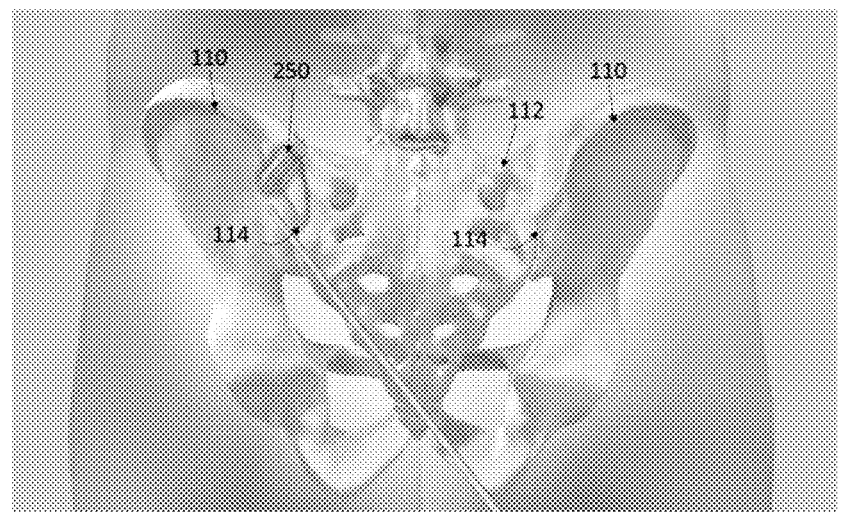
FIG. 26 is a perspective posterior view of the pelvic region with the intra-articular implant of the sacroiliac joint stabilization system of FIG. 2.

As shown in FIG. 26, spacing of subsequent intra-articular implants 250 is performed according to the desired application, number of implants, and position of other implants of sacroiliac joint stabilization system 200. For example, while the C-arm of the fluoroscopy system is in an outlet view at approximately 15-25 degrees oblique outlet cephalad, intra-articular introducer 256 is inserted from within the dissected field at a desired position and trajectory based on predetermined implant spacing. From a lateral view, the angulation of intra-articular introducer 256 is verified. Intra-articular introducer 256 may be advanced as shown in FIG. 18. The process for insertion of other intra-articular implants 250 follows the same steps shown and described by FIG. 17 through FIG. 25, though locations differ.

In FIGS. 27 through 36, a variety of implant and screw positions, numbers, and trajectories are depicted, each compatible with the methods described herein for sacroiliac joint stabilization system 200. In each of these schematics, the outline with several points represents sacroiliac joint 114, with sacrum 112 depicted and ilium 110 not depicted. The shaded region represents the target insertion zone 130 for both intra-articular implants 250 and transfixing implants 210. Dashed arrows represent the insertion path of implants, while intra articular-implants 250 are denoted with solid lines and transfixing implants 210 with dotted circles. All implants are countersunk approximately 5 mm to 10 mm. The view of each schematic is a lateral view from a patient laying prone on a surface, with apex of the sacrum 120 inferior to base of sacrum 118.

Figure 27:
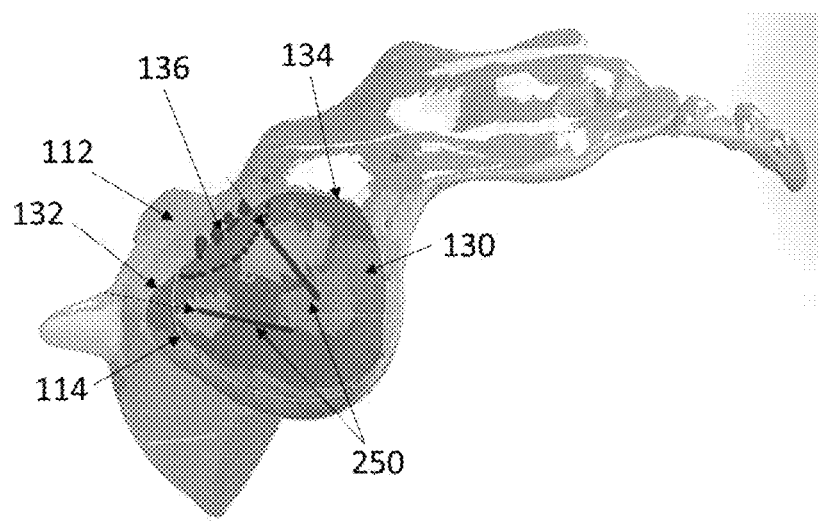
FIG. 27 is a perspective lateral view of a target insertion zone for insertion of two intra-articular implants of the sacroiliac joint stabilization system of FIG. 2.

In FIG. 27, two intra-articular implants 250 are implanted according to the description for FIGS. 17 through 26. The two intra-articular implants 250 are arranged in a converging orientation within sacroiliac joint 114. The first, or inferior intra-articular implant 250 is positioned within a first void which extends through the articular space midsection 136. Inferior intra-articular implant 250 is first inserted at one angle and later adjusted to the depicted trajectory once clear of PSIS 128. Inferior intra-articular implant 250 is countersunk into the first void at approximately 5 mm to 10 mm and extends anterocaudally within a middle portion of target insertion zone 130. A second or superior intra-articular implant 250 is positioned within a second void which extends through the first articular space crest 132. Superior intra-articular implant 250 extends anterocaudally within the caudal portion of target insertion zone 130.

Figure 28:
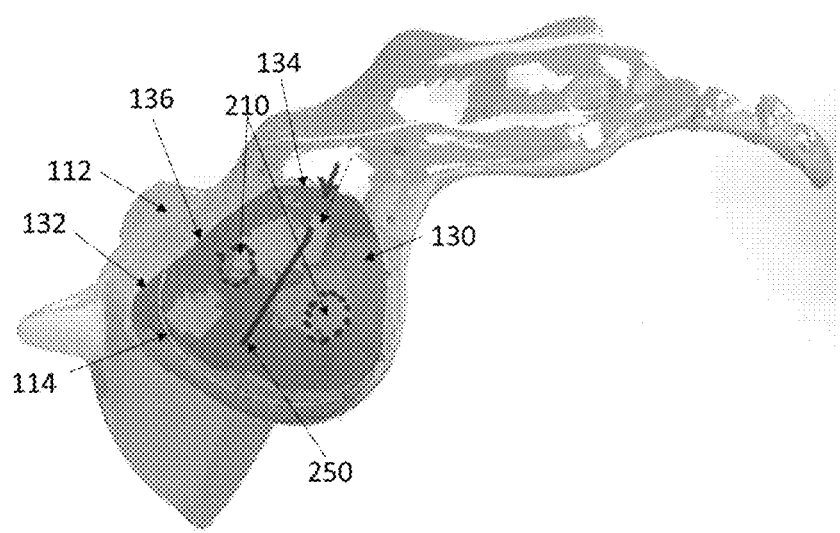
FIG. 28 is a perspective lateral view of the target insertion zone for insertion of one intra-articular implant and two transfixing implants of the sacroiliac joint stabilization system of FIG. 2.

In FIG. 28, two transfixing implants 210 and one intra-articular implant 250 are implanted according to the description for FIGS. 4 through 26. In a preferred embodiment, transfixing implants 210 are 9.5 mm diameter implants, though other sized transfixing implants 210 are possible. Transfixing implants 210 are inserted using an oblique approach within the middle region of target insertion zone 130, with the superior transfixing implant 210 located at just anterior to articular space midsection 136 near PSIS 128. The inferior transfixing implant 210 is located within the middle portion of target insertion zone anterocaudal from the superior transfixing implant 210 and intra-articular implant 250. Intra-articular implant 250 is positioned within a void which extends through the middle portion of target insertion zone 130 from second articular space crest 134 to first articular space crest 132. Intra-articular implant 250 is countersunk into the void at approximately 5 mm to 10 mm and extends anterocranially within a middle portion of target insertion zone 130, approximate bisecting transfixing implants 210.

Figure 29:
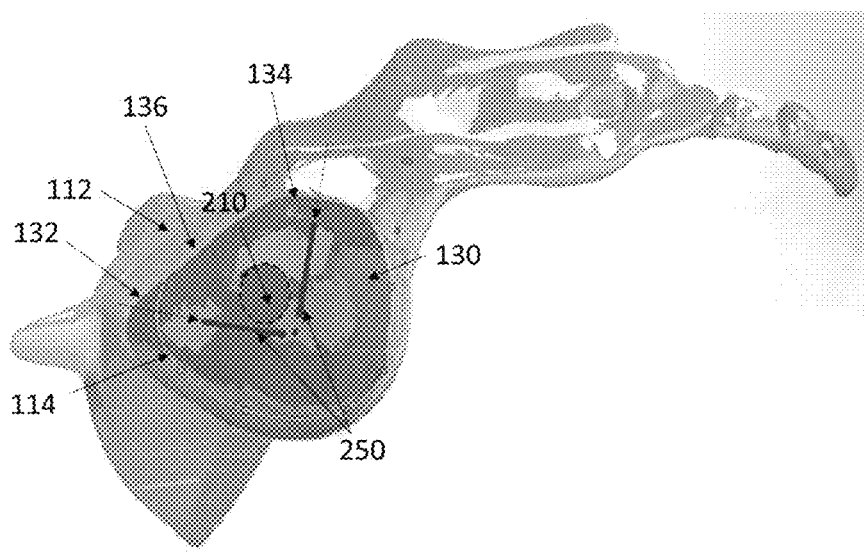
FIG. 29 is a perspective lateral view of the target insertion zone for insertion of two intra-articular implants and one transfixing implant of the sacroiliac joint stabilization system of FIG. 2.

In FIG. 29, two intra-articular implants 250 and one transfixing implant 210 are implanted according to the description for FIGS. 4 through 26. The two intra-articular implants 250 are arranged in a converging orientation and form approximately perpendicular paths within sacroiliac joint 114. The first, or inferior intra-articular implant 250 is positioned within a first void which extends through second articular space crest 134. Inferior intra-articular implant 250 is countersunk into the first void at approximately 5 mm to 10 mm and extends anterocranially within a middle portion of target insertion zone 130. A second or superior intra-articular implant 250 is positioned within a second void which extends through the first articular space crest 132. Superior intra-articular implant 250 extends anterocaudally within the middle portion of target insertion zone 130. The placements of intra-articular implants 250 are approximately perpendicular, and form a "V" in which transfixing implant 210 is located. For placement of transfixing implant 210, insertion is directed at and below the S1 foramen frame, with transfixing implant 210 occupying a location near the convergence of intra-articular implants 250 within the "V". Transfixing implant 210 has a length of less than 50 mm, and preferably less than 45 mm. For instance, transfixing implant 210 is a 9.5 mm diameter and 45 mm length implant or a 7 mm diameter and 35 mm length implant.

Figure 30:
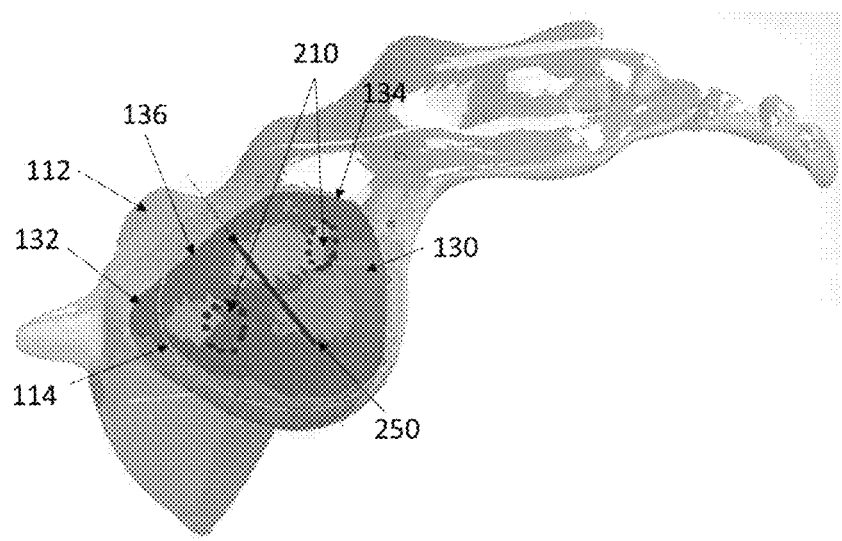
FIG. 30 is a perspective lateral view of the target insertion zone for insertion of one intra-articular implant and two transfixing implants of the sacroiliac joint stabilization system of FIG. 2.

Now referring to FIG. 30, two transfixing implants 210 and one intra-articular implant 250 are implanted according to the description for FIGS. 4 through 26. Intra-articular implant 250 is inserted through articular space midsection 136 and aimed for the apex of sacroiliac joint 114, advancing straight downward at an anterocaudal angle into the middle portion of target insertion zone 130 and leaving adequate space for subsequent insertion of transfixing implants 210. Intra-articular implant 250 is countersunk into its void at approximately 5 mm to 10 mm and extends within the middle portion of target insertion zone 130 to eventually bisect transfixing implants 210. Transfixing implants 210 are generally larger diameter implants, such as greater than or equal to 9.5 mm diameter implants. However, alternatively-sized transfixing implants 210 are possible. The inferior transfixing implant 210 is located within the caudal target insertion zone 130, anterior from second articular space crest 134. The superior transfixing implant 210 is located within the cephalad target insertion zone 130, anterior from first articular space crest 132. Each of the transfixing implants 210 are approximately equidistant from intra-articular implant 250.

Figure 31:
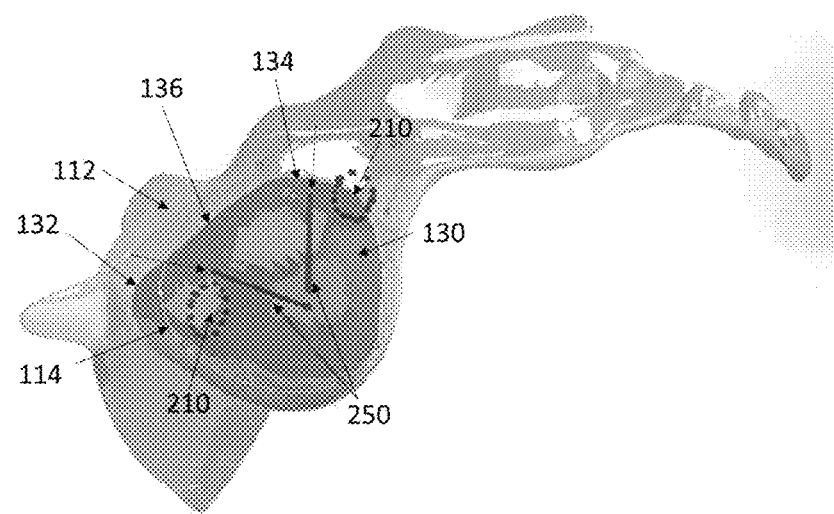
FIG. 31 is a perspective lateral view of the target insertion zone for insertion of two intra-articular implants and two transfixing implants of the sacroiliac joint stabilization system of FIG. 2.

In FIG. 31, two intra-articular implants 250 and two transfixing implants 210 are implanted according to the description for FIGS. 4 through 26. The two intra-articular implants 250 are arranged in a converging orientation and form approximately perpendicular paths within sacroiliac joint 114. The first, or inferior intra-articular implant 250 is positioned within a first void which extends through second articular space crest 134. Inferior intra-articular implant 250 is countersunk into the first void at approximately 5 mm to 10 mm and extends anterocranially within caudle and middle portions of target insertion zone 130. A second or superior intra-articular implant 250 is positioned within a second void which extends through the first articular space crest 132. Superior intra-articular implant 250 extends anterocaudally within cephalad and middle portions of target insertion zone 130. The placements of intra-articular implants 250 are approximately perpendicular, and form a "V" outside of which transfixing implants 210 are located. For placement of transfixing implants 210, insertion is directed at a location outside the "V" formed by intra-articular implants 250. Inferior transfixing implant 210 is inserted within a first void extending through the caudal portion and boundary of target surgical zone 130. The placement is near and inferior to the posterior end of the inferior intra-articular implant 250. Superior transfixing implant 210 is inserted within a second void extending through the cephalad portion of target surgical zone 130. The placement is near and superior to the posterior end of the superior intra-articular implant 250. Transfixing implants are typically large diameter implants, with diameters ranging from approximately 9.5 mm to 13 mm. However, alternatively-sized diameters are possible.

Figure 32:
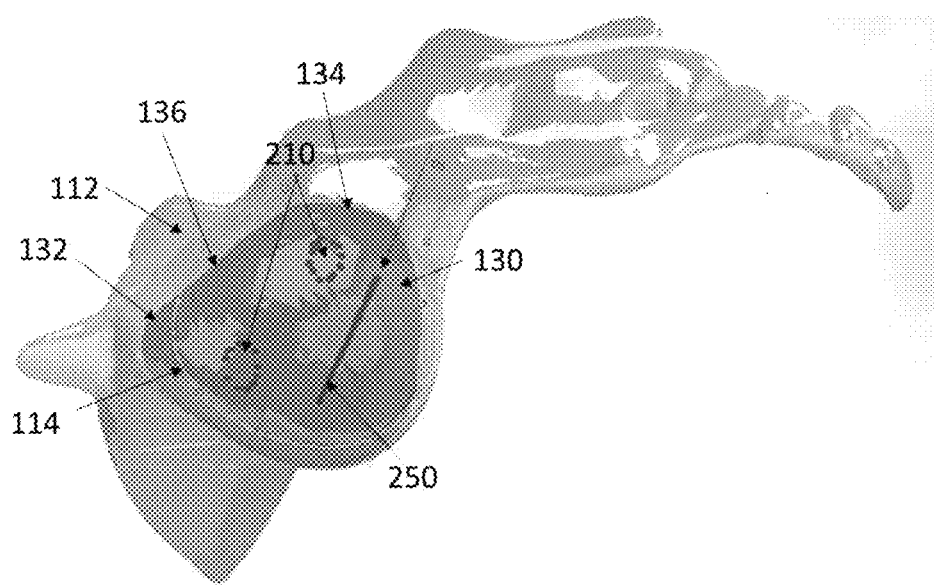
FIG. 32 is a perspective lateral view of the target insertion zone for insertion of one intra-articular implant and two transfixing implants of the sacroiliac joint stabilization system of FIG. 2.

In FIG. 32, two transfixing implants 210 and one intra-articular implant 250 are implanted according to the description for FIGS. 4 through 26. Intra-articular implant 250 is inserted through a caudal portion of second articular space crest 134 and through the middle portion of target insertion zone 130, leaving adequate posterocranial space for transfixing implants 210. Intra-articular implant 250 is countersunk into its void at approximately 5 mm to 10 mm and extends within the middle portion of target insertion zone 130. Transfixing implants 210 are generally larger diameter implants, such as greater than or equal to 9.5 mm diameter implants. However, alternatively-sized transfixing implants 210 are possible. The inferior transfixing implant 210 is located within the caudal target insertion zone 130, anterior to second articular space crest 134. The superior transfixing implant 210 is located within the cephalad target insertion zone 130, anterior to first articular space crest 132. Each of the transfixing implants 210 are located posterocranial to and approximately equidistant from intra-articular implant 250.

Figure 33:
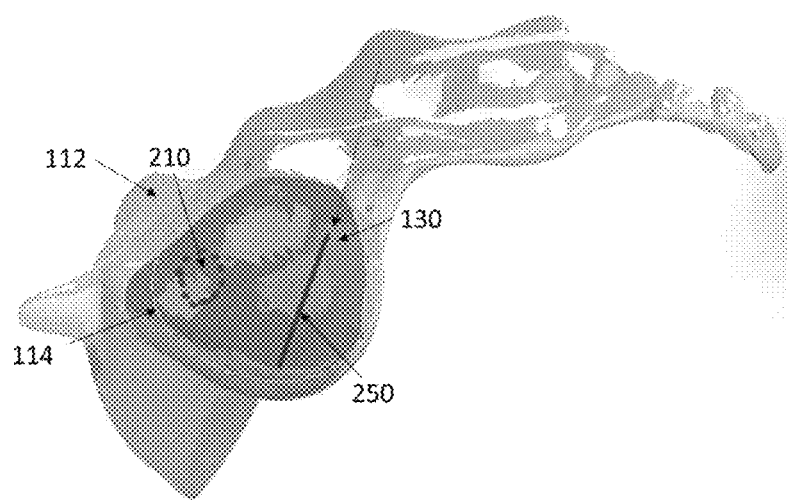
FIG. 33 is a perspective lateral view of the target insertion zone for insertion of one intra-articular implant and one transfixing implant of the sacroiliac joint stabilization system of FIG. 2.

Referring to FIG. 33, there is provided one transfixing implant 210 and one intra-articular implant 250 that are implanted according to the description for FIGS. 4 through 26. Intra-articular implant 250 is inserted through a caudal portion of target surgical zone 130 that is anterocaudal to second articular space crest 134. It is inserted across the middle portion of target insertion zone 130, leaving adequate posterocranial space for transfixing implant 210. Intra-articular implant 250 is countersunk into its void at approximately 5 mm to 10 mm and extends within the middle portion of target insertion zone 130. Transfixing implant 210 is generally a larger diameter implant, such as greater than or equal to 9.5 mm in diameter. In a preferred embodiment, transfixing implant is a 13 mm diameter screw with a length of 40 mm to 80 mm. However, alternatively-sized transfixing implants 210 are possible. Transfixing implant 210 is depicted as located within the cephalad target insertion zone 130, anterior from first articular space crest 132 and posterocranial to intra-articular implant 250. However, transfixing implant 210 may be inserted in any location through target surgical zone 130 such that it does not impede or coincide with intra-articular implant 250.

Figure 34:
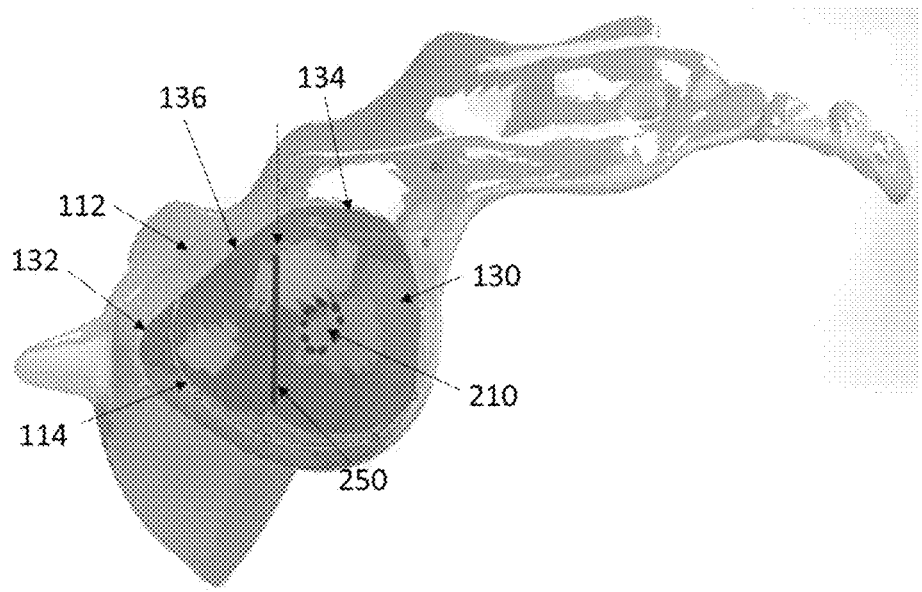
FIG. 34 is a perspective lateral view of the target insertion zone for insertion of one intra-articular implant and one transfixing implant of the sacroiliac joint stabilization system of FIG. 2.

Now referring to FIG. 34, there is provided one transfixing implant 210 and one intra-articular implant 250 that are implanted according to the description for FIGS. 4 through 26. Intra-articular implant 250 is inserted through articular space midsection 136 and into the middle portion of target insertion zone 130, leaving adequate caudal space for transfixing implant 210. Intra-articular implant 250 is countersunk into its void at approximately 5 mm to 10 mm and extends within the middle portion of target insertion zone 130. Transfixing implant 210 is generally a larger diameter implant, such as greater than or equal to 7 mm in diameter. However, alternatively-sized transfixing implants 210 are possible. Transfixing implant 210 is depicted as located within the middle portion of target insertion zone 130, anterior from articular space midsection 136 and caudal to intra-articular implant 250. However, transfixing implant 210 may be inserted in any location through target surgical zone 130 such that it does not impede or coincide with intra-articular implant 250.

Figure 35:
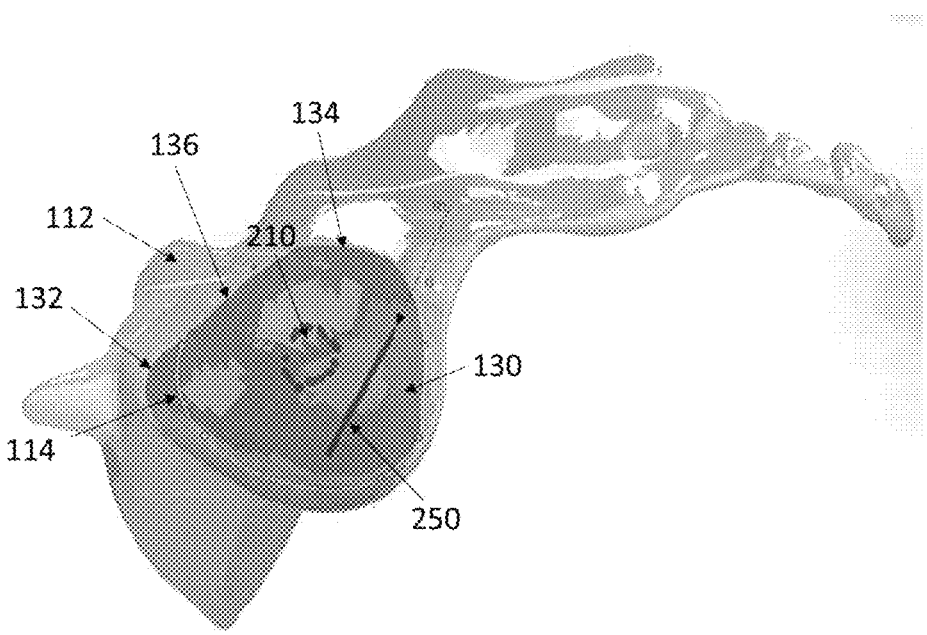
FIG. 35 is a perspective lateral view of the target insertion zone for insertion of one intra-articular implant and one transfixing implant of the sacroiliac joint stabilization system of FIG. 2.

In FIG. 35, there is provided one transfixing implant 210 and one intra-articular implant 250 that are implanted according to the description for FIGS. 4 through 26. Intra-articular implant 250 is inserted through a caudal portion of target surgical zone 130 that is anterocaudal to second articular space crest 134. It is inserted across the middle portion of target insertion zone 130, leaving adequate posterocranial space for transfixing implant 210. Intra-articular implant 250 is countersunk into its void at approximately 5 mm to 10 mm and extends within the middle portion of target insertion zone 130. Transfixing implant 210 is generally a larger diameter implant, such as greater than or equal to 7 mm in diameter. However, alternatively-sized transfixing implants 210 are possible. Transfixing implant 210 is depicted as located within the middle portion of target insertion zone 130, anterior to articular space midsection 136 and posterocranial to intra-articular implant 250. However, transfixing implant 210 may be inserted in any location through target surgical zone 130 such that it does not impede or coincide with intra-articular implant 250.

Figure 36:
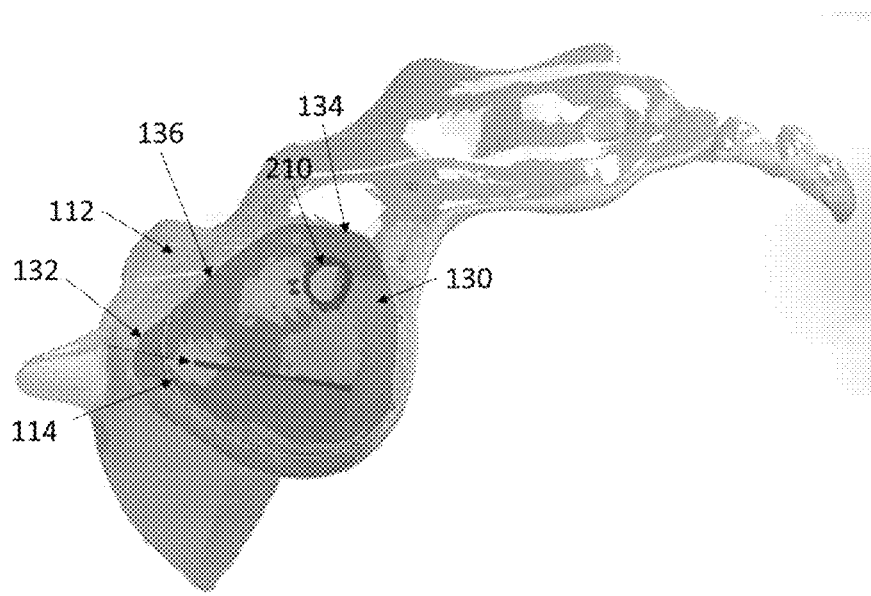
FIG. 36 is a perspective lateral view of the target insertion zone for insertion of one intra-articular implant and one transfixing implant of the sacroiliac joint stabilization system of FIG. 2.

In FIG. 36, there is provided one transfixing implant 210 and one intra-articular implant 250 that are implanted according to the description for FIGS. 4 through 26. Intra-articular implant 250 is inserted through a cranial portion of target surgical zone 130 that is anterior to first articular space crest 132. It is inserted across the cephalad and middle portions of target insertion zone 130, leaving adequate posterocaudal space for transfixing implant 210. Intra-articular implant 250 is countersunk into its void at approximately 5 mm to 10 mm and extends within the cephalad and middle portions of target insertion zone 130. Transfixing implant 210 is generally a larger diameter implant, such as greater than or equal to 7 mm in diameter. However, alternatively-sized transfixing implants 210 are possible. Transfixing implant 210 is depicted as located within the caudal portion of target insertion zone 130, anterior to second articular space crest 134 and posterocaudal to intra-articular implant 250.

As will be apparent to one skilled in the art, various modifications can be made within the scope of the aforesaid description. Such modifications being within the ability of one skilled in the art form a part of the present invention and are embraced by the claims below.

I claim:

1. A method of stabilizing a sacroiliac joint of a patient through a hybrid lateral-posterior approach, the method comprising:
    a) making a first incision for a lateral approach, the first incision located anterior to a posterior sacral wall and inferior to an ala as viewed from a lateral view of a pelvic region of the patient in prone position;
    b) forming a first initial void between the first incision and a lateral aspect of an ilium;
    c) advancing a lateral introducer through the first initial void, through the ilium, across a sacroiliac joint, and into a sacrum;
    d) forming a first intermediate void that is larger in diameter than the first initial void, the first intermediate void formed by advancing at least one lateral dilator over the lateral introducer to the lateral aspect of the ilium;
    e) forming a first final void extending from the first intermediate void, through the ilium and sacroiliac joint, and into the sacrum, the first final void having a sacral extension depth appropriate for reception of a transfixing implant;
    f) placing the transfixing implant within the first final void, such that the transfixing implant extends across the sacroiliac joint with its distal end within the sacrum and its proximal end flush with the lateral aspect of the ilium;
    g) making a second incision for a posterior approach, the second incision located along a lateral border of the sacroiliac joint as viewed from an anterior-posterior view of the pelvic region of the patient in prone position;
    h) forming a second initial void between the second incision and the sacroiliac joint;
    i) advancing an intra-articular introducer through the second initial void and into the sacroiliac joint;
    j) forming a second intermediate void that is larger in diameter than the second initial void, the second intermediate void formed by advancing at least one intra-articular dilator over the intra-articular introducer and into the sacroiliac joint;
    k) forming a second final void that expands the second intermediate void within the sacroiliac joint, the second final void having a sacroiliac joint extension depth appropriate for reception of an intra-articular implant; and
    l) placing the intra-articular implant within the second final void, such that the intra-articular implant extends into the sacroiliac joint, and such that the sacroiliac joint is stabilized by the transfixing implant and the intra-articular implant.

2. The method of claim 1, wherein the transfixing implant extends through a posterocranial region of the sacroiliac joint and the intra-articular implant extends posterocaudal to anterocranial within the sacroiliac joint.

3. The method of claim 1, wherein the transfixing implant extends through a middle region of the sacroiliac joint and the intra-articular implant extends posterior to anterior within the sacroiliac joint.

4. The method of claim 1, wherein the transfixing implant extends through a middle region of the sacroiliac joint and the intra-articular implant extends posterocaudal to anterocranial within the sacroiliac joint.

5. The method of claim 1, wherein the transfixing implant extends through a posterocaudal region of the sacroiliac joint and the intra-articular implant extends posterocranial to anterocaudal within the sacroiliac joint.

6. The method of claim 1, wherein more than one transfixing implants are placed by repeating step a) through f) for each transfixing implant.

7. The method of claim 6, wherein a superior transfixing implant extends through a posterior region of the sacroiliac joint, an inferior transfixing implant extends through an anterior region of the sacroiliac joint, and the intra-articular implant extends posterocaudal to anterocranial within the sacroiliac joint, bisecting the superior and inferior transfixing implants.

8. The method of claim 6, wherein a superior transfixing implant extends through a posterocranial region of the sacroiliac joint, an inferior transfixing implant extends through a posterocaudal region of the sacroiliac joint, and the intra-articular implant extends posterior to anterior within the sacroiliac joint, bisecting the superior and inferior transfixing implants.

9. The method of claim 6, wherein a superior transfixing implant extends through a posterocranial region of the sacroiliac joint, an inferior transfixing implant extends through a posterocaudal region of the sacroiliac joint, and the intra-articular implant extends posterocaudal to anterocranial within the sacroiliac joint.

10. The method of claim 6, wherein more than one intra-articular implants are placed by repeating step g) through l) for each intra-articular implant.

11. The method of claim 10, wherein a superior transfixing implant extends through a posterocranial region of the sacroiliac joint, an inferior transfixing implant extends through a posterocaudal region of the sacroiliac joint, a superior intra-articular implant extends posterocranial to anterocaudal within the sacroiliac joint, and an inferior intra-articular implant extends posterocaudal to anterocranial within the sacroiliac joint, the intra-articular implants converging at their distal ends.

12. The method of claim 1, wherein more than one intra-articular implants are placed by repeating step g) through l) for each intra-articular implant.

13. The method of claim 12, wherein the transfixing implant extends through a posterior region of the sacroiliac joint, a superior intra-articular implant extends posterocranial to anterocaudal within the sacroiliac joint, and an inferior intra-articular implant extends posterocaudal to anterocranial within the sacroiliac joint, the intra-articular implants converging at their distal ends and the transfixing implant located posterior to the converging distal ends.

14. A method of stabilizing a sacroiliac joint of a patient through a hybrid lateral-posterior approach, the method comprising:
   a) making a first incision for a posterior approach, the first incision located along a lateral border of a sacroiliac joint as viewed from an anterior-posterior view of a pelvic region of the patient in prone position;
   b) forming a first initial void between the first incision and the sacroiliac joint;
   c) advancing an intra-articular introducer through the first initial void and into the sacroiliac joint;
   d) forming a first intermediate void that is larger in diameter than the first initial void, the first intermediate void formed by advancing at least one intra-articular dilator over the intra-articular introducer and into the sacroiliac joint;
   e) forming a first final void that expands the first intermediate void within the sacroiliac joint, the first final void having a sacroiliac joint extension depth appropriate for reception of an intra-articular implant; and
   f) placing the intra-articular implant within the first final void, such that the intra-articular implant extends into the sacroiliac joint;
   g) making a second incision for a lateral approach, the second incision located anterior to a posterior sacral wall and inferior to an ala as viewed from a lateral view of the pelvic region of the patient in prone position;
   h) forming a second initial void between the second incision and a lateral aspect of an ilium;
   i) advancing a lateral introducer through the second initial void, through the ilium, across the sacroiliac joint, and into a sacrum;
   j) forming a second intermediate void that is larger in diameter than the second initial void, the second intermediate void formed by advancing at least one lateral dilator over the lateral introducer to the lateral aspect of the ilium;
   k) forming a second final void extending from the second intermediate void, through the ilium and sacroiliac joint, and into the sacrum, the second final void having a sacral extension depth appropriate for reception of a transfixing implant;
   l) placing the transfixing implant within the second final void, such that the transfixing implant extends across the sacroiliac joint with its distal end within the sacrum and its proximal end flush with the lateral aspect of the ilium, and such that the sacroiliac joint is stabilized by the transfixing implant and the intra-articular implant.

15. A lateral-posterior approach sacroiliac joint stabilizing method comprising:
   forming a first incision that is anterior to a posterior sacral wall and inferior to an ala and a second incision that is located along a lateral border of the sacroiliac joint,
   forming a first void that extends from the first incision, through an ilium, across a sacroiliac joint and into a sacrum and a second void that extends from the second incision and into the sacroiliac joint, and
   placing a first implant within the first void such that the first implant extends across the sacroiliac joint with a distal end thereof within the sacrum and a proximal end thereof flush with a lateral aspect of the ilium, and a second implant within the second void such that the second implant extends into the sacroiliac joint.

16. The method of claim 15, wherein the first implant extends through a posterocranial region of the sacroiliac joint and the second implant extends posterocaudal to anterocranial within the sacroiliac joint.

17. The method of claim 15, wherein the first implant extends through a middle region of the sacroiliac joint and the second implant extends posterior to anterior within the sacroiliac joint.

18. The method of claim 15, wherein the first implant extends through a middle region of the sacroiliac joint and the second implant extends posterocaudal to anterocranial within the sacroiliac joint.

19. The method of claim 15, wherein the first implant extends through a posterocaudal region of the sacroiliac joint and the second implant extends posterocranial to anterocaudal within the sacroiliac joint.

20. The method of claim 15, wherein the first implant is configured for receiving and containing bone shaving therewithin.

* * * * *